(12) United States Patent
Cooper et al.

(10) Patent No.: US 12,616,538 B2
(45) Date of Patent: *May 5, 2026

(54) ARTICULATABLE MEMBERS HAVING CONSTRAINED MOTION AND RELATED DEVICES AND METHODS

(71) Applicant: INTUITIVE SURGICAL OPERATIONS, INC., Sunnyvale, CA (US)

(72) Inventors: Thomas G. Cooper, Menlo Park, CA (US); Matthew R. Williams, Walnut Creek, CA (US); William John Park, San Jose, CA (US)

(73) Assignee: Intuitive Surgical Operations, Inc., Sunnyvale, CA (US)

( * ) Notice: Subject to any disclaimer, the term of this patent is extended or adjusted under 35 U.S.C. 154(b) by 919 days.

This patent is subject to a terminal disclaimer.

(21) Appl. No.: 17/460,977

(22) Filed: Aug. 30, 2021

(65) Prior Publication Data

US 2022/0054208 A1     Feb. 24, 2022

Related U.S. Application Data

(63) Continuation of application No. 15/118,620, filed as application No. PCT/US2015/015849 on Feb. 13, 2015, now Pat. No. 11,109,925.

(Continued)

(51) Int. Cl.
*A61B 17/00* (2006.01)
*A61B 18/14* (2006.01)
(Continued)

(52) U.S. Cl.
CPC ........ *A61B 34/35* (2016.02); *A61B 17/00234* (2013.01); *A61B 18/14* (2013.01);
(Continued)

(58) Field of Classification Search
CPC . A61B 2017/00314–00323; A61B 1/008–009; A61B 1/005–0051; A61B 1/0055; A61B 1/0057
See application file for complete search history.

(56) References Cited

U.S. PATENT DOCUMENTS

| | | | |
|---|---|---|---|
| 4,661,944 A | 4/1987 | Van Sluys | |
| 5,916,147 A | 6/1999 | Boury | |

(Continued)

FOREIGN PATENT DOCUMENTS

| | | |
|---|---|---|
| CN | 101394975 A | 3/2009 |
| CN | 101516273 A | 8/2009 |

(Continued)

OTHER PUBLICATIONS

Extended European Search Report for Application No. 15751972.9, mailed on Aug. 17, 2017, 17 pages.

(Continued)

*Primary Examiner* — Jaymi E Della
(74) *Attorney, Agent, or Firm* — Jones Burke, PLLC

(57) ABSTRACT

An articulatable member includes a distal end, a proximal end, an actuation member, and a constraint member. The actuation member extends from the proximal end to the distal end. The actuation member transmits force to bend the articulatable member from a neutral position. The constraint member extends from the proximal end to the distal end. The constraint member may have opposite ends that are fixed to the distal end and the proximal end. In one embodiment, the constraint member follows a helical path along at least a portion of the articulatable member from the proximal end to the distal end. In another embodiment, the actuation member follows a helical path along at least a portion of the articulatable member.

20 Claims, 19 Drawing Sheets

Related U.S. Application Data

(60) Provisional application No. 61/943,106, filed on Feb. 21, 2014.

(51) Int. Cl.

| | |
|---|---|
| *A61B 34/00* | (2016.01) |
| *A61B 34/30* | (2016.01) |
| *A61B 34/35* | (2016.01) |
| *B25J 9/10* | (2006.01) |

(52) U.S. Cl.
CPC .............. *A61B 34/30* (2016.02); *A61B 34/71* (2016.02); *B25J 9/104* (2013.01); *A61B 2017/00314* (2013.01); *A61B 2034/306* (2016.02)

(56) References Cited

U.S. PATENT DOCUMENTS

| | | | |
|---|---|---|---|
| 6,817,974 | B2 | 11/2004 | Cooper et al. |
| 7,320,700 | B2 | 1/2008 | Cooper et al. |
| 7,608,083 | B2 | 10/2009 | Lee et al. |
| 7,942,868 | B2 | 5/2011 | Cooper et al. |
| 8,069,747 | B2 * | 12/2011 | Buckingham ............ B25J 18/06 |
| | | | 901/15 |
| 8,545,515 | B2 | 10/2013 | Prisco et al. |
| 8,608,647 | B2 | 12/2013 | Durant et al. |
| 8,887,595 | B2 | 11/2014 | Williams |
| 8,911,428 | B2 | 12/2014 | Cooper et al. |
| 9,060,678 | B2 | 6/2015 | Larkin et al. |
| 11,109,925 | B2 | 9/2021 | Cooper et al. |
| 2006/0094931 | A1 | 5/2006 | Danitz et al. |
| 2008/0065099 | A1 | 3/2008 | Cooper et al. |
| 2008/0065105 | A1 | 3/2008 | Larkin et al. |
| 2008/0065106 | A1 | 3/2008 | Larkin |
| 2008/0177283 | A1 | 7/2008 | Lee et al. |
| 2009/0099420 | A1 | 4/2009 | Woodley et al. |
| 2009/0299333 | A1 | 12/2009 | Wendlandt et al. |
| 2009/0326714 | A1 | 12/2009 | Buckingham et al. |
| 2010/0228284 | A1 | 9/2010 | Cooper et al. |
| 2011/0152879 | A1 | 6/2011 | Williams |
| 2011/0196419 | A1 | 8/2011 | Cooper |
| 2012/0209253 | A1 | 8/2012 | Donhowe |
| 2012/0220831 | A1 | 8/2012 | Cooper et al. |
| 2013/0012928 | A1 | 1/2013 | Cooper et al. |
| 2013/0041403 | A1 | 2/2013 | Cunningham et al. |
| 2013/0144116 | A1 | 6/2013 | Cooper et al. |

FOREIGN PATENT DOCUMENTS

| | | |
|---|---|---|
| CN | 102905627 A | 1/2013 |
| JP | S63501000 A | 4/1988 |
| JP | 2009522121 A | 6/2009 |
| WO | WO-2004052171 A2 | 6/2004 |
| WO | WO-2007077458 A1 | 7/2007 |
| WO | WO-2007120353 A2 | 10/2007 |
| WO | WO-2007146987 A2 | 12/2007 |
| WO | WO-2008033240 A2 | 3/2008 |
| WO | WO-2011060315 A2 | 5/2011 |
| WO | WO-2011119399 A1 | 9/2011 |
| WO | WO-2015127231 A1 | 8/2015 |

OTHER PUBLICATIONS

International Search Report and Written Opinion for Application No. PCT/US15/15849, mailed on May 21, 2015, 19 pages.

Office Action mailed Jul. 19, 2018 for Chinese Application No. 201580019171.1 filed Feb. 13, 2015, 12 pages.

Office Action mailed Feb. 3, 2020 for Chinese Application No. 201580019171.1 filed on Feb. 13, 2015, 17 pages.

Rosheim, Mark E., Chapter 5: "Pitch-Yaw-Roll Wrists," Robot Wrist Actuators, Wiley & Sons, New York, 1989, pp. 95-206.

Salle D., et al., "Surgery Grippers for Minimally Invasive Heart Surgery," Proceeding of IEEE International Conference on Intelligent Manipulation and Grasping (IMG 04), Jul. 2004, 8 pages.

Vertut, J, and Coiffet, P., "Robot Technology: Teleoperation and Robotics Evolution and Development," English translation, Prentice-Hall, Inc., Inglewood Cliffs, NJ, USA 1986, vol. 3A, 332 pages.

Extended European Search Report for Application No. EP24160603.7, mailed on May 22, 2024, 11 pages.

Extended European Search Report for Application No. EP25182804.2, mailed on Aug. 19, 2025, 14 pages.

\* cited by examiner

240

250

252

254

260

290

270

280

263

265

PROXIMAL ◄──────► DISTAL

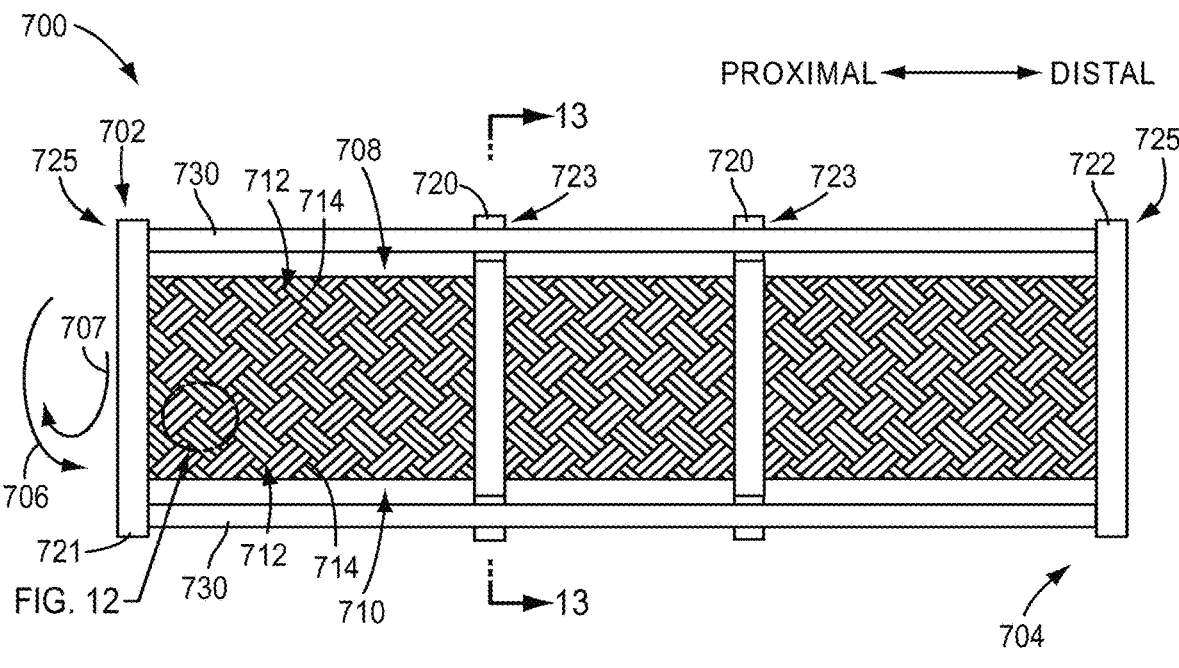
FIG. 11
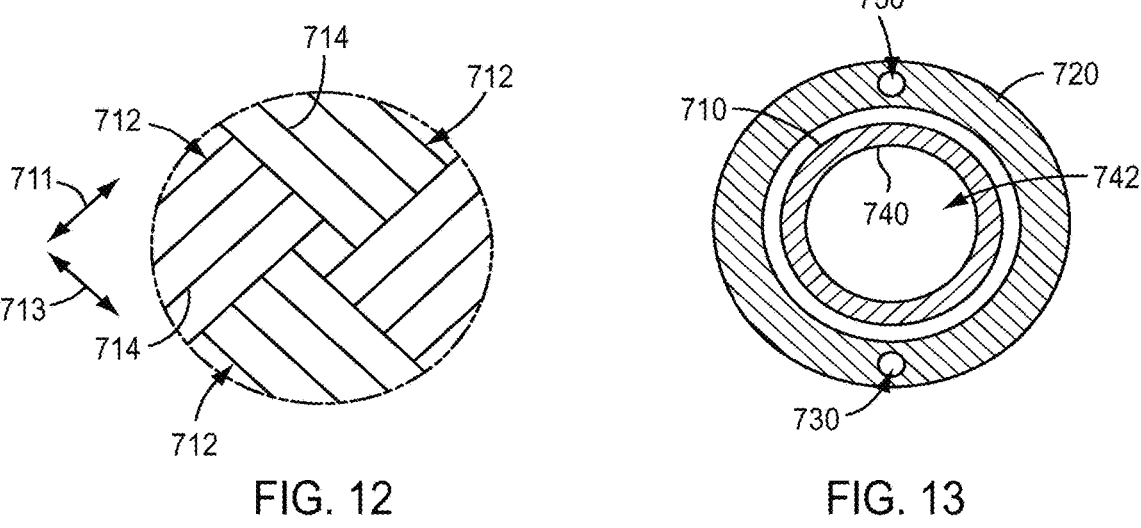
FIG. 12                    FIG. 13

ARTICULATABLE MEMBERS HAVING CONSTRAINED MOTION AND RELATED DEVICES AND METHODS

This application is a continuation application of application Ser. No. 15/118,620, filed Aug. 12, 2016 (now U.S. Pat. No. 11,109,925), which is a U.S. national phase of international application no. PCT/US2015/015849, filed Feb. 13, 2015, which designated the United States and claimed right of priority to U.S. provisional application No. 61/943,106, filed Feb. 21, 2014 (now expired), each of which are incorporated herein by reference in their entirety.

TECHNICAL FIELD

Aspects of the present disclosure relate to articulatable members that exhibit constrained motion. More particularly, aspects of the present disclosure relate to surgical instruments, and related systems and methods, utilizing such articulatable members.

BACKGROUND

Remotely controlled surgical instruments, which can include teleoperated surgical instruments as well as manually operated (e.g., laparoscopic, thorascopic) surgical instruments, are often used in minimally invasive medical procedures. During medical procedures, an instrument may be articulated to position a portion of the instrument in a desired location. Positioning of the instrument in a desired location or orientation can be achieved by constraining the motion of one or more joints of the instrument. However, mechanisms to constrain the motion of one or more joints of an instrument can increase the mechanical complexity and operation of an instrument, and increase the difficulty of manufacturing an instrument.

The overall size of minimally invasive surgical instruments may pose constraints on the design of surgical instruments. In various applications, it is desirable for the overall size, including the outer lateral dimensions (e.g., diameter), of such instruments to be relatively small to fit within narrow lumens and other passages. In some cases, therefore, it is desirable to select the number and placement of force transmission elements so as to reduce the overall size of the instruments. For example, the number and placement of force transmission elements that interconnect a series of articulably coupled links to provide actuation forces to control bending of the links may be such that the one or more force transmission elements pass through one or more links without directly attaching and terminating at such links. For example, the bending and steering of a plurality of joints (or link pairs) in a series may be actuated through a single force transmission element (or single set of force transmission elements in the case of multiple bend directions and or degrees of freedom (DOFs)) without each joint or link pair being capable of individual direct bending by actuation of a force transmission element directly attached to such a link pair. Such a configuration is sometimes referred to as "underconstrained." In other words, the steering and bending of multiple link pairs is actuated by a single force transmission element or single set of force transmission elements that is attached to and terminates at a link of one of the link pairs. Such "underconstrained" structures, however, can pose challenges in attempting to controllably steer and bend the structure, thereby potentially resulting in unpredictable and/or uncontrollable movement (articulation) of the links.

Control systems and other mechanisms have been proposed to assist in constraining the movement of otherwise underconstrained jointed link structures. However, a need exists to provide alternate designs for articulatable members that achieve constrained motion so as to be able to accurately control movement and positioning of the articulatable member.

SUMMARY

Exemplary embodiments of the present disclosure may solve one or more of the above-mentioned problems and/or may demonstrate one or more of the above-mentioned desirable features. Other features and/or advantages may become apparent from the description that follows.

In accordance with at least one exemplary embodiment, an articulatable member comprises a distal end, a proximal end, an actuation member, and a constraint member. The actuation member may extend from the proximal end to the distal end. The actuation member may transmit force to bend the articulatable member from a neutral position. The constraint member may extend from the proximal end to the distal end. The constraint member may have opposite ends that are fixed to the distal end and the proximal end, respectively. Further, the constraint member may follow a helical path along at least a portion of the articulatable member from the proximal end to the distal end.

In accordance with another exemplary embodiment, an articulatable member may comprise a proximal end, a distal end, an actuation member, and a constraint member. The actuation member may extend from the proximal end to the distal end. The actuation member may be configured to transmit force to bend the articulatable member from a neutral position. The constraint member may extend from the proximal end to the distal end. The constraint member may have opposite ends that are fixed to the distal end and the proximal end, respectively. Further, the actuation member may follow a helical path along at least a portion of the articulatable member between the proximal end and the distal end of the articulatable member.

In accordance with another exemplary embodiment, a surgical instrument comprises a shaft, a force transmission mechanism connected to a proximal end of the shaft, a parallel motion mechanism connected to a distal end of the shaft, a wrist, an actuation member, and a constraint member. The wrist may comprise a plurality of links and be coupled to a distal end of the parallel motion mechanism. The actuation member may transmit force from the force transmission mechanism to bend the articulatable member from a neutral position or bend the wrist from a neutral position. The constraint member may extend through at least the wrist. The constraint member may passively constrain motion of the wrist mechanism. Opposite ends of the constraint member may be respectively fixed to a proximal end and a distal end of the wrist.

Additional objects, features, and/or advantages will be set forth in part in the description which follows, and in part will be obvious from the description, or may be learned by practice of the present disclosure and/or claims. At least some of these objects and advantages may be realized and attained by the elements and combinations particularly pointed out in the appended claims.

It is to be understood that both the foregoing general description and the following detailed description are exemplary and explanatory only and are not restrictive of the claims; rather the claims should be entitled to their full breadth of scope, including equivalents.

BRIEF DESCRIPTION OF THE DRAWINGS

The present disclosure can be understood from the following detailed description, either alone or together with the accompanying drawings. The drawings are included to provide a further understanding of the present disclosure, and are incorporated in and constitute a part of this specification. The drawings illustrate one or more exemplary embodiments of the present teachings and together with the description serve to explain certain principles and operation.

FIG. 11 is a side view of a wrist including a braided structure, according to an exemplary embodiment.

FIG. 12 is an enlarged view of area FIG. 12 in FIG. 11.

FIG. 13 is a view along line 13-13 in FIG. 11.

DETAILED DESCRIPTION

Figure 1A:
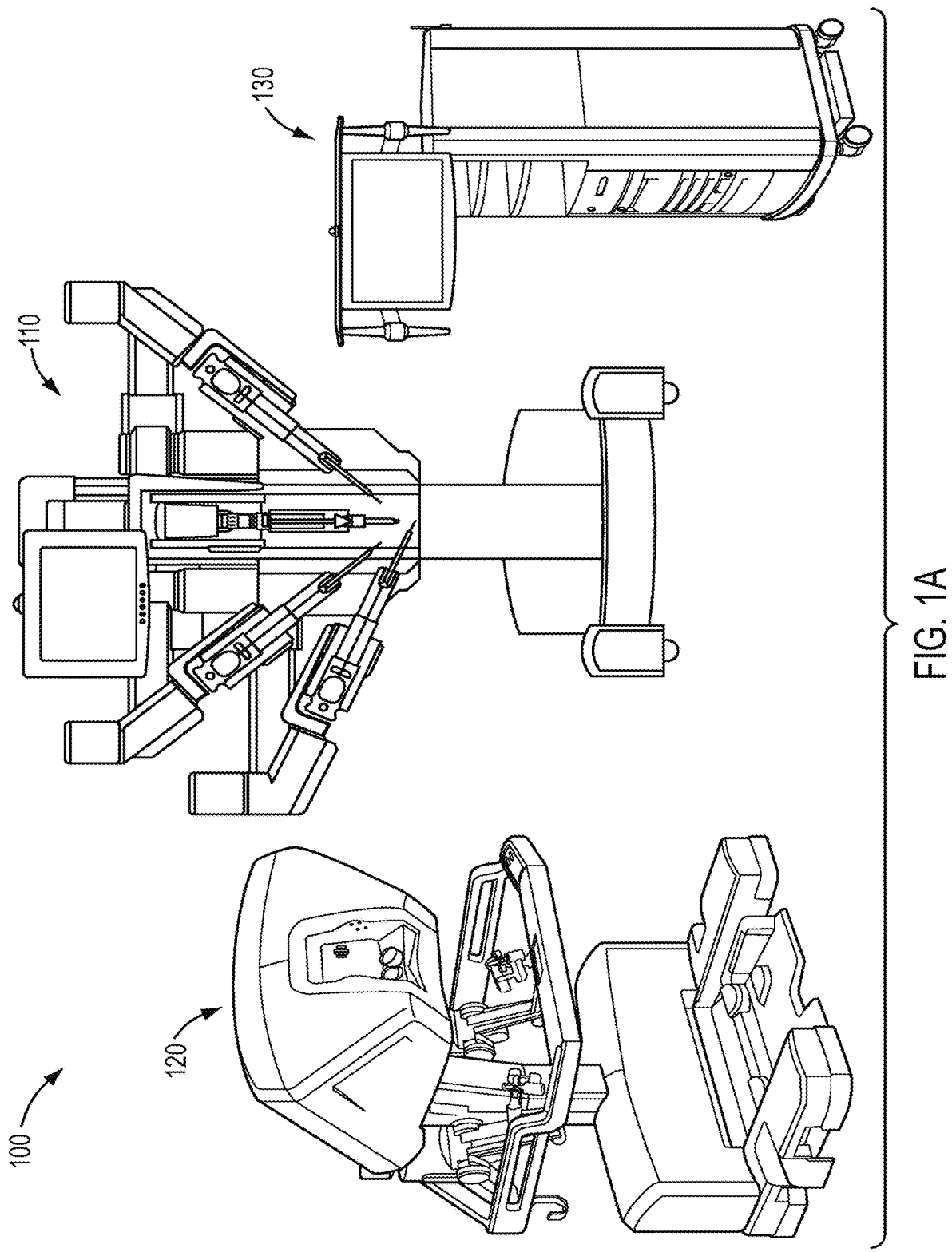
FIG. 1A shows a teleoperated surgical system, according to an exemplary embodiment.

This description and the accompanying drawings that illustrate exemplary embodiments should not be taken as limiting. Various mechanical, compositional, structural, electrical, and operational changes may be made without departing from the scope of this description and the claims, including equivalents. In some instances, well-known structures and techniques have not been shown or described in detail so as not to obscure the disclosure. Like numbers in two or more figures represent the same or similar elements. Furthermore, elements and their associated features that are described in detail with reference to one embodiment may, whenever practical, be included in other embodiments in which they are not specifically shown or described. For example, if an element is described in detail with reference to one embodiment and is not described with reference to a second embodiment, the element may nevertheless be claimed as included in the second embodiment.

For the purposes of this specification and appended claims, unless otherwise indicated, all numbers expressing quantities, percentages, or proportions, and other numerical values used in the specification and claims, are to be understood as being modified in all instances by the term "about," to the extent they are not already so modified. Accordingly, unless indicated to the contrary, the numerical parameters set forth in the following specification and attached claims are approximations that may vary depending upon the desired properties sought to be obtained. At the very least, and not as an attempt to limit the application of the doctrine of equivalents to the scope of the claims, each numerical parameter should at least be construed in light of the number of reported significant digits and by applying ordinary rounding techniques.

It is noted that, as used in this specification and the appended claims, the singular forms "a," "an," and "the," and any singular use of any word, include plural referents unless expressly and unequivocally limited to one referent. As used herein, the term "include" and its grammatical variants are intended to be non-limiting, such that recitation of items in a list is not to the exclusion of other like items that can be substituted or added to the listed items.

Further, this description's terminology is not intended to limit the disclosure or claims. For example, spatially relative terms-such as "beneath", "below", "lower", "above", "upper", "proximal", "distal", and the like-may be used to describe one element's or feature's relationship to another element or feature as illustrated in the orientation of the figures. These spatially relative terms are intended to encompass different positions (i.e., locations) and orientations (i.e., rotational placements) of a device in use or operation in addition to the position and orientation shown in the figures. For example, if a device in the figures is inverted, elements described as "below" or "beneath" other elements or features would then be "above" or "over" the other elements or features. Thus, the exemplary term "below" can encompass both positions and orientations of above and below. A device may be otherwise oriented (rotated 90 degrees or at other orientations) and the spatially relative descriptors used herein interpreted accordingly. The relative proximal and distal directions of surgical instruments are labeled in the figures.

In various instruments with articulatable members, such as jointed link structures, movement of the articulatable member is constrained by actively controlling the movement of the components of the articulatable member (e.g., disks). Actuation members, such as drive tendons or drive rods, used to articulate the articulatable member may also be used to actively constrain the movement of the articulatable member. For instance, the actuation members may be coupled to a force transmission mechanism, such as a gimbal cable actuator described in U.S. Pat. No. 6,817,974, and coupled to disks of a jointed link structure so that force transmitted to the actuation members via the force transmission mechanism may be used to move the disks and articulate the jointed link structure. This configuration may also be used to actively constrain the movement of the disks, such as by transmitting force from the force transmission mechanism to the actuation members to hold the disks in place.

In some cases, instruments that actively constrain movement via actuation members utilize a relatively large number of actuation members to accurately control the movement of the articulatable member when the articulatable member is articulated or its movement is constrained. For example, a wrist may include additional joints to increase the range of motion of the wrist. However, this may result in additional actuation members to actuate and/or constrain the additional joints, thereby increasing the complexity and cost of the wrist, particularly when the joints are actively constrained. Moreover, particularly for instruments having a smaller diameter, it is generally desirable to use fewer actuation members so as to conserve space within the instrument. Aside from their number, the nature of actively controlled constraint members (e.g., actuation members that are used to actively constrain the movement of an articulatable member using forces applied to the actuation members) can increase the complexity of a wrist due to the mechanisms used to apply a force to the actuation members. Therefore, it may be desirable to provide constraint members that are not actively constrained.

Various exemplary embodiments of the present disclosure contemplate articulatable members in which the movement of the articulatable members is passively constrained. In other words, movement of the articulatable member is constrained without the use of an actuator, such as a force transmission mechanism and control algorithms controlling the same. For example, in various exemplary embodiments, the movement of disks of a jointed link structure is passively constrained by constraint members that are not actuatable by an external drive or transmission mechanism, but rather are reactive to motion (articulation) of the jointed link structure itself. According to an exemplary embodiment, the constraint members may be fixed at opposite ends of the jointed link structure. As a result, the constraint members need not utilize force transmission mechanisms to actively constrain movement of the articulatable member, which permits the use of fewer actuation members and potentially less complex force transmission mechanisms. Further, ends of the constraint members may be secured at the opposite ends of the articulatable member. Thus, the constraint members need not extend to a proximal end of an instrument where actuators, such as a force transmission mechanism, are located, thereby conserving space along an instrument shaft proximal to the articulatable member. Further, by not extending constraint members through the lumen (e.g., shaft) of an instrument to the proximal end of the instrument, the internal space of the lumen may be easier to clean because there are fewer objects within the lumen.

In accordance with various exemplary embodiments, the present disclosure contemplates articulatable members for instruments that include mechanisms to constrain the motion of the articulatable members. The constraint mechanisms may be secured at opposite ends of the articulatable member, which may be a wrist, a parallel motion mechanism, or other articulatable member used in an instrument. In various exemplary embodiments the articulatable members are jointed link structures. In one exemplary embodiment of a wrist of an instrument, the constraint mechanisms extend along a helical path along at least a portion of the length of the wrist. The wrist may further include actuation members, such as drive tendons, that extend substantially straight through the wrist. The wrist may include a series of connected disks that pivot about rotational axes that alternate in different directions (e.g., orthogonal) or that pivot about at least two consecutive rotational axes extending in substantially the same direction. A constraint mechanism is not limited to a tendon or a rod but instead may be, for example a braided structure, which may be used to provide the structure of an articulatable member, such as by replacing the disks of a jointed link structure. Alternatively, a braided structure can be used to constrain the motion of disks of a jointed link structure. In a parallel motion mechanism, the constraint mechanisms may extend substantially straight through the parallel motion mechanism, while drive tendons for the parallel motion mechanism extend along a helical path as they extend through at least a portion of the length of the parallel motion mechanism. According to an exemplary embodiment, when an instrument includes both a wrist and a parallel motion mechanism, a constraint mechanism can be used to constrain the motion of at least the wrist or both the wrist and the parallel motion mechanism. In another example, separate constraint mechanisms can be used to respectively constrain the motion of the wrist and the parallel motion mechanism.

Figure 1B:
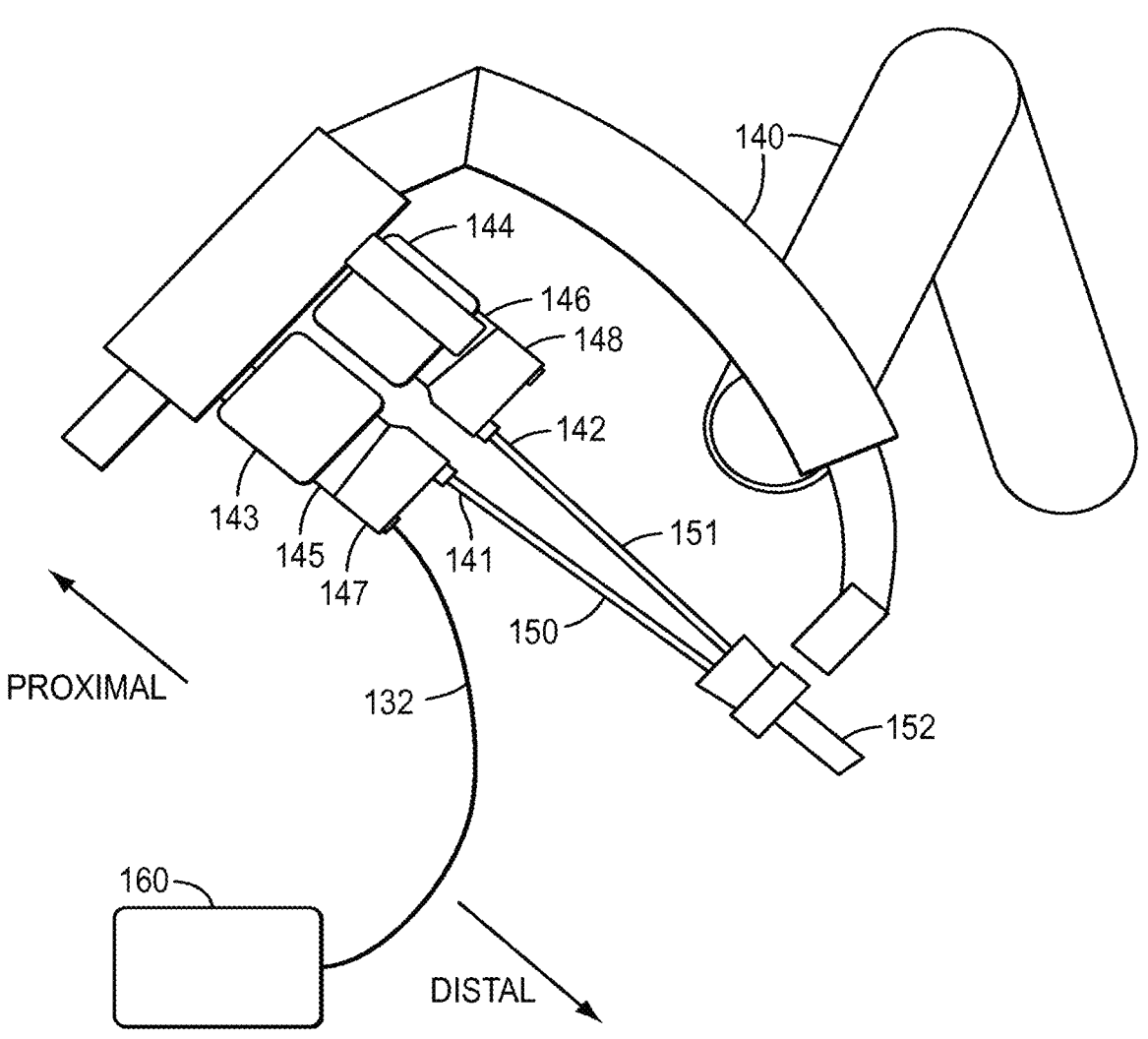
FIG. 1B shows a portion of a manipulator arm of a patient side cart, according to an exemplary embodiment.

Referring now to FIG. 1A, an exemplary embodiment of a teleoperated surgical system 100 is shown, which includes a patient side cart 110, a surgeon console 120 for receiving input from a user to control instruments of patient side cart 110, and an auxiliary control/vision cart 130. System 100, which may, for example, be a da Vinci® Surgical System, da Vinci® Si (model no. IS3000), Single Site da Vinci® Surgical System, or a da Vinci® Xi Surgical System available from Intuitive Surgical, Inc. However, various other teleoperated surgical system configurations may be used with the exemplary embodiments described herein. Referring now to the schematic illustration of FIG. 1B, a portion of an exemplary embodiment of a manipulator arm 140 of a patient side cart with two surgical instruments 141, 142 in an installed position is shown. The schematic illustration of FIG. 1B depicts only two surgical instruments for simplicity, but more than two surgical instruments may be received in an installed position at a patient side cart as those having ordinary skill in the art are familiar with. Each surgical instrument 141, 142 includes an instrument shaft 150, 151 that at a distal end has a moveable end effector (discussed below in regard to FIG. 2) or a camera or other sensing device, and may or may not include a wrist mechanism (discussed below in regard to FIG. 2) to control the movement of the distal end.

In the exemplary embodiment of FIG. 1B, the distal end portions of the surgical instruments 141, 142 are received through a single port structure 152 to be introduced into the patient. Other configurations of patient side carts that can be used in conjunction with the present disclosure can use several individual manipulator arms. In addition, individual manipulator arms may include a single instrument or a plurality of instrument. Further, an instrument may be a surgical instrument with an end effector or may be a camera instrument or other sensing instrument utilized during a surgical procedure to provide information, (e.g., visualization, electrophysiological activity, pressure, fluid flow, and/or other sensed data) of a remote surgical site.

Force transmission mechanisms 147, 148 are disposed at a proximal end of each shaft 150, 151 and connect through a sterile adaptor 145, 146 with actuation interface assemblies 143, 144. Actuation interface assemblies 143, 144 contain a variety of mechanisms (discussed further below with regard to the exemplary embodiment of FIG. 2) that are controlled by a controller (e.g., at a control cart of a surgical system) to respond to input commands at a surgeon side console of a surgical system to transmit forces to the force transmission mechanisms 147, 148 to actuate instruments 141, 142.

The diameter or diameters of an instrument shaft, wrist, and end effector are generally selected according to the size of the cannula with which the instrument will be used and depending on the surgical procedures being performed. In various exemplary embodiments, a shaft and/or wrist about 3 mm, 4 mm, 5 mm, 6 mm, 7 mm, or 8 mm in diameter, for example, to be inserted in some existing cannula systems; however, larger instrument sizes are also considered as within the scope of the present disclosure. According to an exemplary embodiment, depending on the type of surgical instrument, one or more of surgical instruments 141, 142 may be in communication with a flux source 160 via a flux transmission conduit 132. For example, if a surgical instrument 141 is an electrosurgical instrument, flux transmission conduit 132 is an electrical energy transmission cable and flux source 160 is an electrical energy generator.

Figure 2:
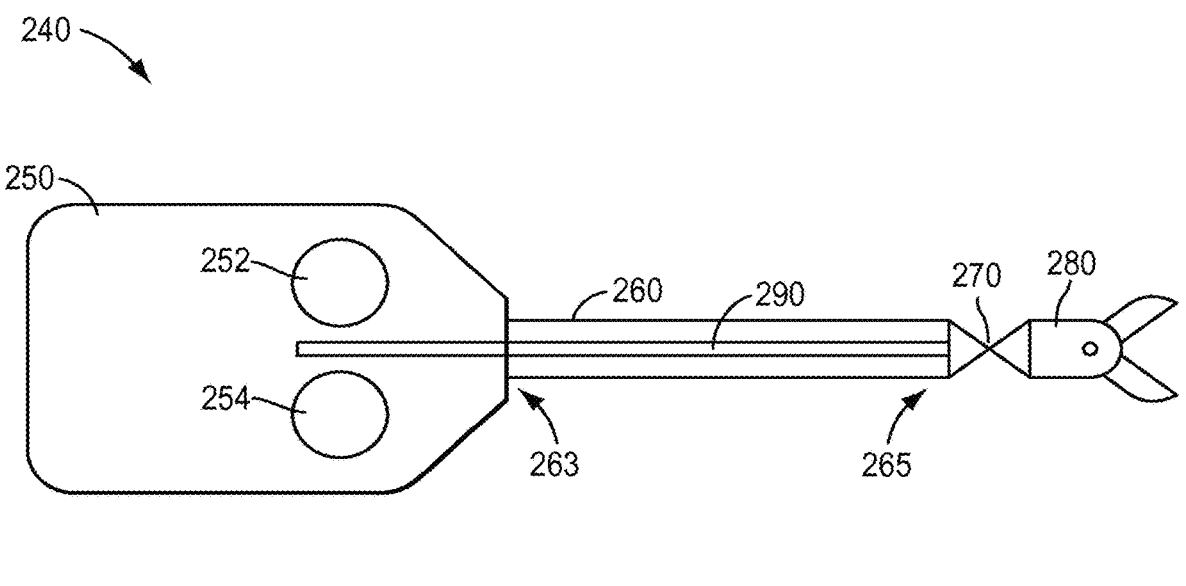
FIG. 2 is a top view of an exemplary embodiment of a surgical instrument including a force transmission mechanism.

Turning to FIG. 2, a bottom schematic view of a surgical instrument 240 is shown, according to an exemplary embodiment. Surgical instrument 240 may include a force transmission mechanism 250, a shaft 260 connected to force transmission mechanism 250 at a proximal end 263 of shaft 260, and an end effector 280 connected to a distal end 265 of shaft 260. According to an exemplary embodiment, end effector 280 may be coupled to the distal end 265 of shaft 260 via a wrist 270, as shown in FIG. 2. Wrist 270 may be actuated in one or more degrees of freedom (DOF's) (e.g., pitch, yaw, roll) to position end effector 280 at a desired location.

Instrument 240 may include other joints, such as a parallel motion mechanism (not shown) positioned between distal end 265 of shaft 260 and wrist 270, according to an exemplary embodiment. For further details regarding exemplary parallel motion mechanisms and their functions reference is made to U.S. Pat. No. 7,942,868, issued May 17, 2011, and U.S. Pub. No. US 2008/0065105, published Mar. 13, 2008, both of which are incorporated by reference herein in their entireties.

Surgical instrument 240 may include one or more actuation members to translate force between force transmission mechanism 250 and end effector 280 and between force transmission mechanism 250 and wrist 270 and/or a parallel motion mechanism (not shown). For instance, one or more actuation member(s) 290 may connect force transmission mechanism 250 to end effector 280 to provide actuation forces to end effector 280. The actuation members may extend along an interior of shaft 260. By utilizing actuation member(s) 290, force transmission mechanism 250 may actuate end effector 280 to, for example, to control a jaw of end effector 280 (or other moveable part) and/or control wrist 270 of instrument 240. Actuation member(s) 290 may be tension members, such as, for example, cables, wires, or the like, and may actuate the surgical instrument in a pull-pull manner. In another exemplary embodiment, the actuation member(s) 290 can be a compression member, such as, for example, a push rod, or the like, and operate in a push-pull manner, as described in U.S. Pat. No. 8,545,515, issued on Oct. 1, 2013, which is hereby incorporated by reference in its entirety.

Force transmission mechanism 250 may include one or more components to engage with a patient side cart of a teleoperated surgical system to translate a force provided by patient side cart to surgical instrument 240. According to an exemplary embodiment, force transmission mechanism 250 includes one or more driver disks 252, 254 that engage with a patient side manipulator of patient side cart, as described in U.S. Pat. No. 8,545,515. Thus, driver disks 252, 254 utilize actuation forces from a teleoperated (robotic) manipulator to actuate various DOFs of instrument 240, including, but not limited to, for example, roll, pitch, yaw, and/or various end effector movements (e.g., open, close, translate). Force transmission mechanism 250 is not limited to two driver disks 252, 254 and may include fewer or greater numbers of driver disks. For instance, force transmission mechanism 250 may include a number of driver disks corresponding to the number of DOFs of instrument 240, with some disks, or combination of disks, potentially controlling multiple instrument DOFs. In addition, although driver disks 252, 254 are depicted as being substantially parallel to the plane of the page of FIG. 2, which results in the rotational axes (not shown) of driver disks 252, 254 extending substantially perpendicular to the plane of the page of FIG. 4, while shaft 260 extends substantially parallel to the plane of the page of FIG. 4, the embodiments described herein may use force transmission mechanisms that include driver disks arranged in other configurations, such as, for example, driver disks having rotational axes extending substantially parallel to shaft 260.

The diameter or diameters of shaft 260, wrist 270, and end effector 280 for surgical instrument 240, as well as the diameter of a camera instrument, are generally selected according to the size of the cannula with which the instrument will be used. In another exemplary embodiment, a diameter of camera instrument and a diameter of wrist 270 and main shaft 260 may range from about 3 mm to about 10 mm. In another exemplary embodiment, a diameter of camera instrument and a diameter of wrist 270 and main shaft 260 may range from about 5 mm to about 8 mm. For example, the diameter may be about 4 mm, about 5 mm, about 6 mm, about 7 mm, or about 8 mm, for example so as to be sized to be inserted within some existing cannula systems. Further, although instruments may have circular cross-sections, instruments with non-circular cross-sections also are contemplated. For instance, a camera instrument may have an oval-shaped cross-section, such as a cross-section with a major axis having a length of, for example, about 13 mm to about 17 mm, and a minor axis having a length of, for example, about 8 mm to about 10 mm.

Systems and techniques for constraining the movement (bending) of articulatable members, such as wrists, may permit precise control of the movement of an articulatable member by minimizing undesired movement of components of the articulatable member. For instance, a constraint mechanism can minimize movement of disks in unintended directions, which may lead to slipping or dislocation of a disk relative to other disks in a jointed link structure or to an S-shape configuration when an arc shape with a single inflection may be desired.

As discussed above, motion of an articulatable member, such as a wrist, may be actively constrained by connecting a set of actuation elements (e.g., tendons) to one or more force transmission mechanisms, such as force transmission mechanism 250. Various mechanisms in a transmission mechanism of the instrument may be utilized to provide control over the actuation elements and thereby serve to constrain motion of jointed link structures or other articulatable member.

A constraint configuration utilizing sets of cables that terminate at each of a series of disks to actively control motion of disk and that extend to a force transmission mechanism at a proximal end of an instrument can increase the mechanical complexity of an instrument and take up valuable space in smaller instruments that may be used for other components.

In view of these considerations, various exemplary embodiments of the present disclosure contemplate articulatable members that exhibit constrained motion so that articulated movement of the articulatable member is conducted in a relatively repeatable, precise, and smooth manner to position the articulatable members in a desired and predictable configuration. Further, an instrument including an articulatable member in accordance with exemplary embodiments of the present disclosure may have a mechanically less complex force transmission mechanism despite a relatively small overall diameter of the instrument, may be relatively easy to operate, and may be cost efficient to manufacture.

Figure 3:
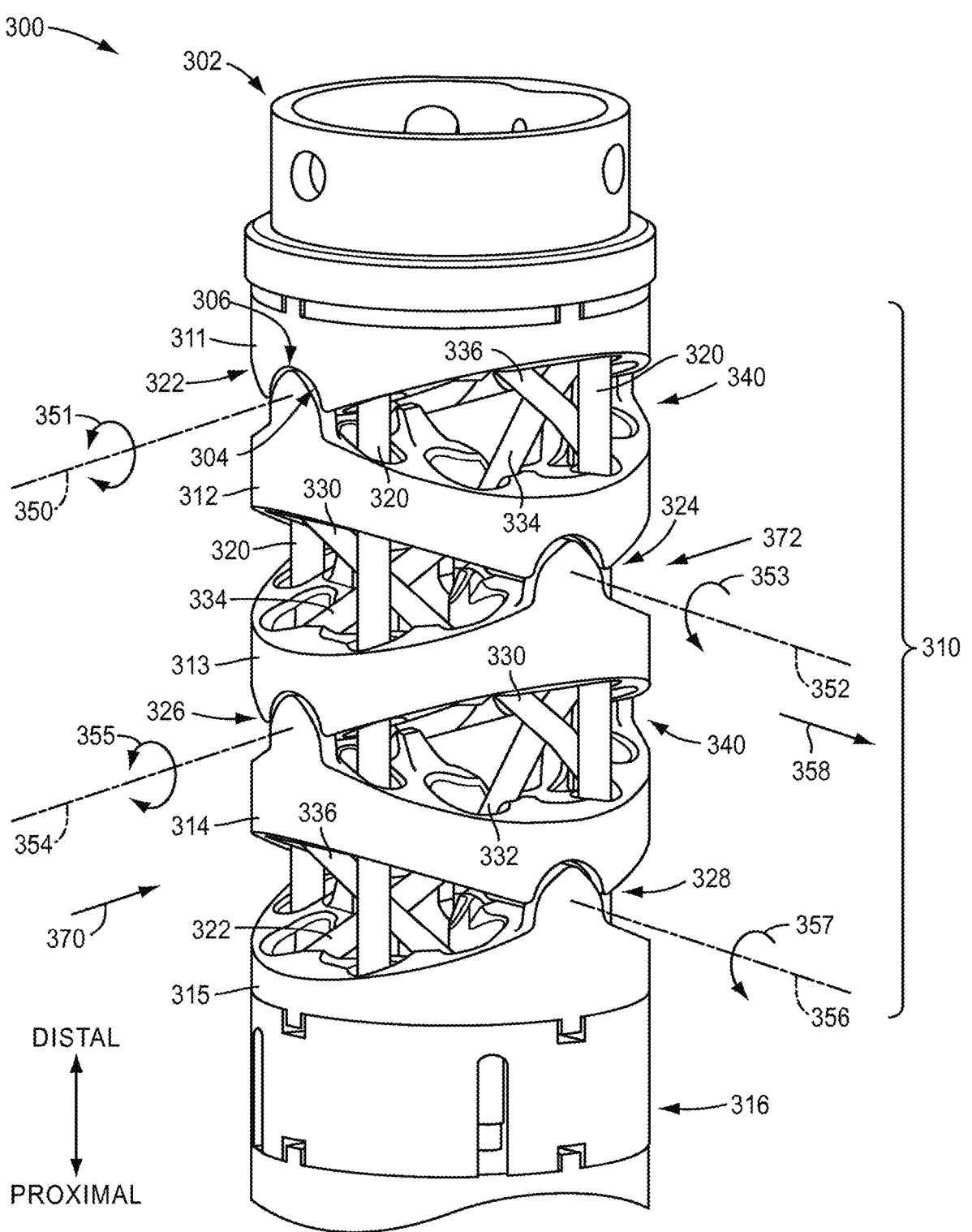
FIG. 3 is a partial view of a distal portion of a surgical instrument including a jointed link structure, according to an exemplary embodiment.

According to an exemplary embodiment, an articulatable member having constrained motion is a jointed link structure used as a wrist in a surgical instrument. Turning to FIG. 3, a distal portion 300 of an instrument shaft is shown. By way of non-limiting example, the surgical instrument may be a camera instrument or a surgical instrument with an end effector supported by a wrist according to the exemplary embodiments of FIG. 2. For instance, an end effector or camera device (not shown) may be connected to a distal end 302 of surgical instrument distal portion 300, which may be, for example, a collar. As shown in FIG. 3, distal portion 300 may include a wrist 310 connected to a portion 316 of an instrument proximal to wrist 310. The portion 316 may be, for example, a distal end of an instrument shaft, according to the exemplary embodiment of FIG. 2, or may be a distal end of a parallel motion mechanism, as will be discussed below. Wrist 310 is a jointed link structure that includes a plurality of disks connected at joints between the disks to provide motion to wrist 310 in arbitrary pitch and/or yaw directions. For instance, wrist 310 may include disks 311-315, although other numbers of disks may be utilized in a wrist, such as seven disks (such as in a wrist mechanism with six joints), eight disks (such as in a wrist with seven joints), or even larger numbers of disks. Although the exemplary embodiments described herein are described as including disks, this is only one possible non-limiting configuration. For instance, links may be used instead of disks for the exemplary embodiments described herein. According to an exemplary embodiment, disks 311-315 may include mechanical stops (not shown) to limit the motion of wrist 310, such as in pitch and/or yaw directions.

As depicted in FIG. 3, wrist 310 further includes a joint 322 providing an axis of rotation 350 between the pair of disks 311 and 312; a joint 324 providing an axis of rotation 352 between the pair of disks 312 and 313; a joint 326 providing an axis of rotation 354 between the pair of disks 313 and 314; and a joint 328 providing an axis of rotation 356 between the pair of disks 314 and 315. The axes 350 and 354 extend in substantially the same direction as each other, and axis 352 and 356 extend in substantially the same direction as each other and in a direction substantially orthogonal to axes 350 and 354. Thus, axes 350, 352, 354, 356 are arranged to provide arbitrary pitch and yaw directional movement of the joints 322, 324, 326, and 328, with axes 350, 352, 354, 356 alternating in differing directions, as shown in FIG. 3. Although joints 322, 324, 326, 328 are depicted in the exemplary embodiment of FIG. 3 as each having a single axis (axes 350, 352, 354, 356 for each of joints 322, 324, 326, 328, respectively) joints 322, 324, 326, 328 may instead include other numbers of axes. For example, joints 322, 324, 326, 328 may articulate according to the exemplary embodiments of U.S. Pat. No. 8,911,428, published Dec. 16, 2014, which is hereby incorporated by reference in its entirety, including the exemplary embodiment of FIG. 25 of U.S. Pat. No. 8,911,428.

As shown in the exemplary embodiment of FIG. 3, one or more actuation elements 320 extend through wrist 310. The actuation elements 320 may be tendons used, for example, to actuate wrist 310, such as by fixing distal ends of actuation elements 320 to a distal end 302 of instrument shaft portion 300 or to disk 311 of wrist 310. In another example, one or more actuation elements 320 may be used to actuate other components of an instrument, such as an end effector of a surgical instrument, such as according to the actuation member 290 and end effector 280 of the exemplary embodiment of FIG. 2. Actuation elements 320 may extend substantially straight as actuation elements 320 through wrist 310, according to an exemplary embodiment, and as illustrated in FIG. 3.

According to an exemplary embodiment, actuation elements 320 may be arranged in pairs that extend through wrist 310, a shaft of an instrument, and to a force transmission mechanism. The force transmission mechanism may include various types of mechanisms to actuate the actuation elements, such as, for example, capstans, gears, levers, gimbals, rack and pinion devices, pulleys, and other devices those having ordinary skill in the art are familiar with. For instance, four actuation elements 320 arranged in two pairs may extend through wrist 310, although other numbers of actuation elements 320 and pairs of actuation elements 320 may be utilized. A pair of actuation elements 320 may be connected to a capstan to actuate actuation elements 320, such as in the form of a pull/pull drive mechanism or a push/pull drive mechanism, as described in U.S. Pat. No. 8,545,515. The capstan may be connected, according to an exemplary embodiment, to one of the interface disks 252, 254 of the force transmission mechanism 250 of the exemplary embodiment of FIG. 2, which transmit forces received from a patient side manipulator of a patient side cart 110 of the exemplary embodiment of FIG. 1A, causing capstan to rotate and actuate actuation elements 320. Other force transmission mechanisms also may be used as those having ordinary skill in the art are familiar with, with the capstans being a non-limiting and exemplary configuration.

Figure 4:
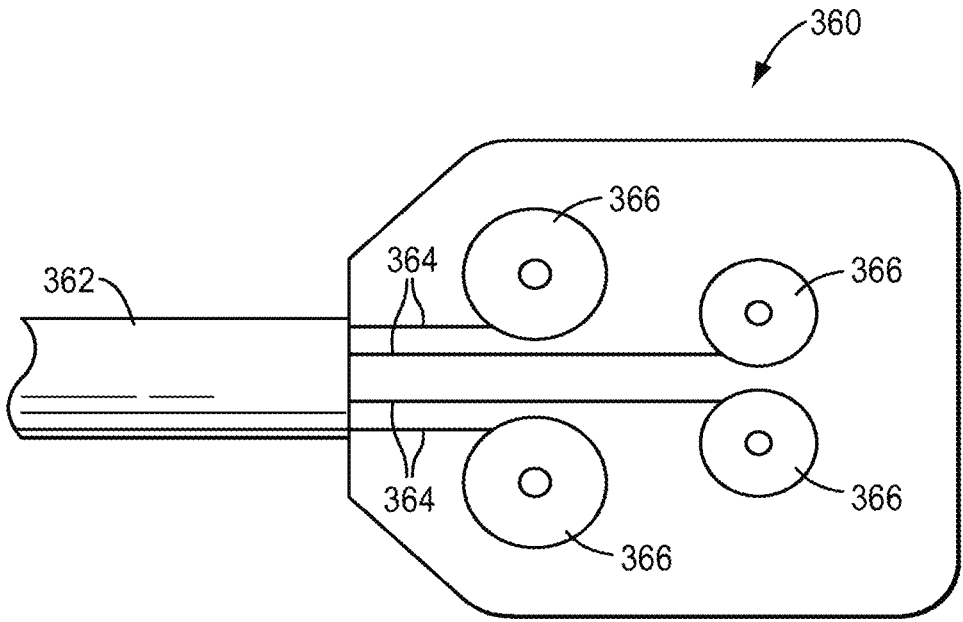
FIG. 4 is a partial top view of a shaft portion and force transmission mechanism of an instrument, according to an exemplary embodiment.

As shown in the exemplary embodiment of FIG. 4, actuation elements 364 may extend through a shaft 362 of an instrument to the force transmission mechanism 360, such as when actuation elements 364 are pull/pull actuation members. In another exemplary embodiment, actuation elements 364 may be push/pull actuation members and capstans 366 may be replaced with gears to drive actuation elements 364. Force transmission mechanism 360 may be configured according to the exemplary embodiment of FIG. 2. For instance, force transmission mechanism 360 may include interface driver disks to actuate capstans 366, similar to interface driver disks 182, 184 of the exemplary embodiment of FIG. 2.

Wrist 310 may include structures to passively constrain the motion of wrist 310. According to an exemplary embodiment, wrist 310 may include one or more constraint tendon(s) that extend through wrist 310. To constrain the motion of wrist 310, constraint tendon(s) may be fixed to the distal and proximal ends of wrist 310. According to an exemplary embodiment, passive constraint tendon(s) may be fixed to ends of an articulatable portion of wrist 310, such as, for example, the articulatable portion provided by disks 311-315. Thus, as will be discussed below, passive constraint tendon(s) may be fixed to, for example, disks 311 and 315 themselves or to positions proximate to disks 311 and 315. When wrist 310 is articulated to bend a desired direction, the constraint tendon(s) will be bent with wrist 310. Because constraint tendon(s) are fixed to the distal and proximal ends of wrist 310, constraint tendon(s) have a fixed length relative to the wrist 310, causing the constraint tendon(s) to passively apply a force to disks 311-315. Thus, if one of disks 311-315 begins to translate in a radial direction relative to the other disks, constraint tendons will act upon the translating disk so as to tend to resist the translation movement and keep the disk aligned along the longitudinal axis of the wrist. For instance, if disk 313 experiences a force that acts to translate disk 313 radially along direction 358 relative to disks 312 and 314, constraint tendons in contact with disk 313, such as by passing through apertures in disk 313, will act on the disk 313 to resist the radial translation along direction 358, thus tending to constrain the translation movement of disk 313.

Figure 5:
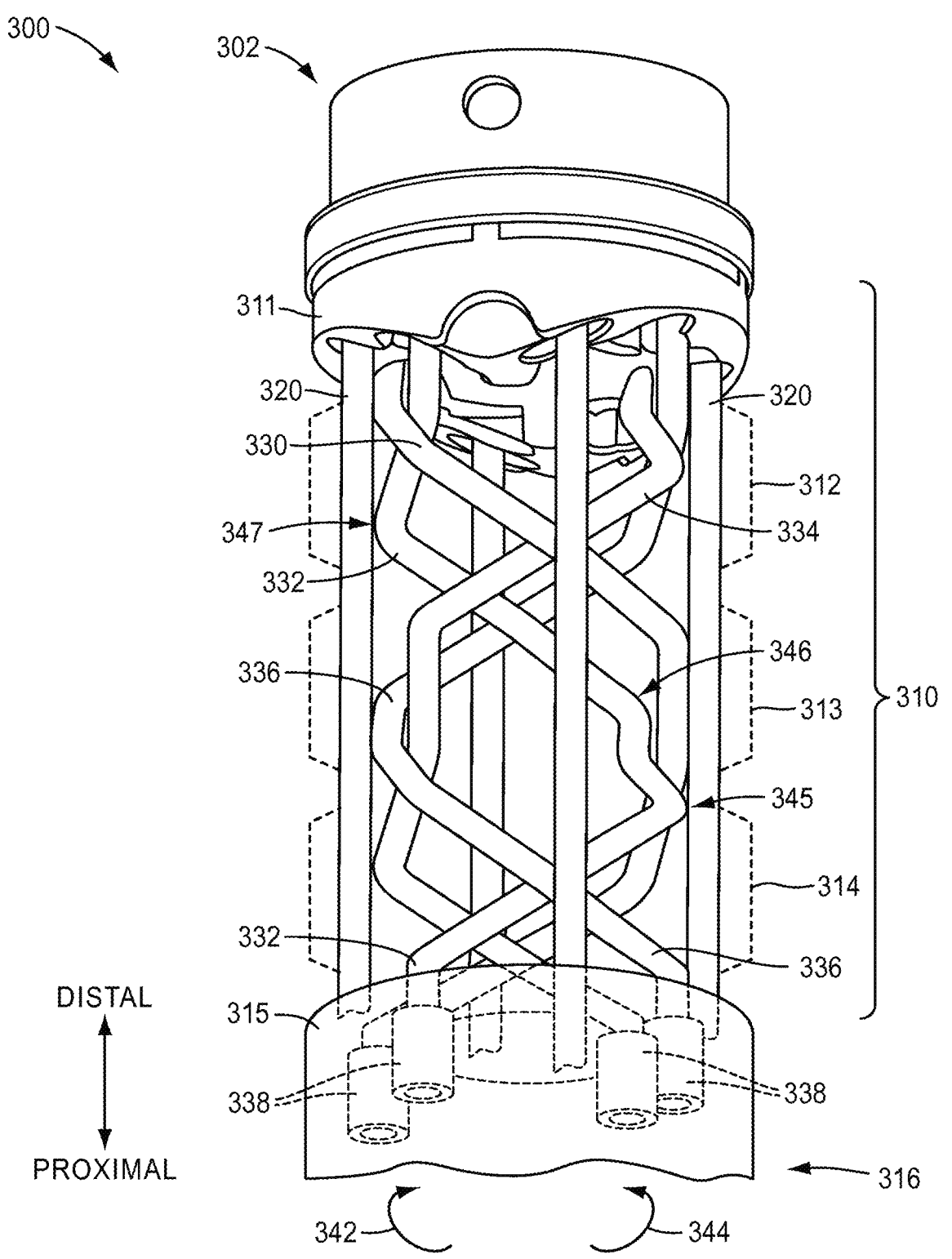
FIG. 5 is the partial view of FIG. 3 with disks removed to reveal internal components.

Constraint tendons may be fixed in place via, for example, welding constraint tendons in place, crimping constraint tendons to another object, or by other methods familiar to one of ordinary skill in the art. For instance, distal ends of constraint tendons may be fixed to disk 311 or to distal end 302 of instrument and proximal ends of constraint tendon(s) may be fixed to disk 315 or to instrument portion 316 proximal to wrist 310. Turning to FIG. 5, which shows distal instrument shaft portion 300 of FIG. 3 but with disks 312-314 represented by only dashed lines to reveal internal components of wrist 310, constraint tendons 330, 332, 334, 336 are each fixed at a proximal end of wrist 310 by a crimp 338, according to an exemplary embodiment. Crimps 338 may be located within passages of disk 315 or instrument portion 316. Distal ends of constraint tendons 330, 332, 334, 336 also can be fixed by crimps (not shown) within passages of disk 311 or distal end 302 of instrument shaft distal portion 300.

According to an exemplary embodiment, constraint tendons may be fixed in place so as to apply a tension to the constraint tendons. A tension applied to a fixed constraint tendon when a wrist is in the substantially straight or neutral configuration as shown in the exemplary embodiment of FIG. 3 (which may also be referred to as a pre-loaded tension) may range, for example, from approximately 0 pounds to 5 pounds, in various exemplary embodiments. When the tension is approximately 0 pounds in the substantially straight or neutral configuration, for example, a constraint tendon may apply a force to the disks of a wrist to constrain motion of the disks once the wrist is articulated. According to another exemplary embodiment, a tension applied to a fixed constraint tendon when a wrist is in the substantially straight or neutral configuration, as shown in the exemplary embodiment of FIG. 3, may range, for example, from approximately 3 pounds to approximately 5 pounds. As constraint tendons are fixed at ends of wrist, according to an exemplary embodiment, constraint tendons do not extend through a shaft of an instrument to a force transmission mechanism and are not actuated by the force transmission mechanism, which may simplify the force transmission mechanism, facilitate control, and conserve instrument space.

According to an exemplary embodiment, constraint tendons may be twisted (e.g., in a substantially helical pattern) through at least a portion of a wrist. Although wrist 310 includes four constraint tendons 330, 332, 334, 336, as shown in the exemplary embodiment of FIG. 5, the present disclosure contemplates other numbers of constraint tendons, such as two, three, five, six, seven, eight, or more constraint tendons. According to an exemplary embodiment, constraint tendons 330, 332, 334, 336 extend along a helical path from disk 315 to disk 311, as shown in FIG. 5, so that each of the constraint tendons 330, 332, 334, 336 traverses a helical path.

According to an exemplary embodiment, constraint tendons of the exemplary embodiments described herein may continuously curve when extending along helical paths and follow a substantially twisted path. For instance, constraint tendons may extend along a helical path with a substantially constant radius of curvature or with a radius of curvature that differs in various sections along the constraint tendons. According to another exemplary embodiment, constraint tendons extending along a helical path may include one or more straight path sections in which the constraint tendons extend substantially straight. For instance, constraint tendons may include straight sections that extend between disks, such as, for example, between each of disks 311-315. Constraint tendons may extend along a helical path by including a series of substantially straight sections angled relative to one another to provide the helical path, according to an exemplary embodiment. According to another exemplary embodiment, constraint tendons may include a mixture of one or more curved sections in which the constraint tendons curve and one or more substantially straight sections. For instance, constraint tendons may be curved when passing through disks and substantially straight between disks. According to an exemplary embodiment, the slope of constraint tendons, as the constraint tendons extend along a longitudinal direction of an instrument, may be substantially constant or may vary. For instance, the slope of constraint tendons may vary from one curved section to another, from one straight section to another, or between straight and curved sections of a constraint tendon as the constraint tendon extends along a longitudinal direction of an instrument. Regardless of whether the helical paths followed by the constraint tendons contain some straight sections or varying degrees of curvature, the helical path can be considered approximately helical such that the constraint tendons extend over some angular extent when projected onto a plane.

Figure 6:
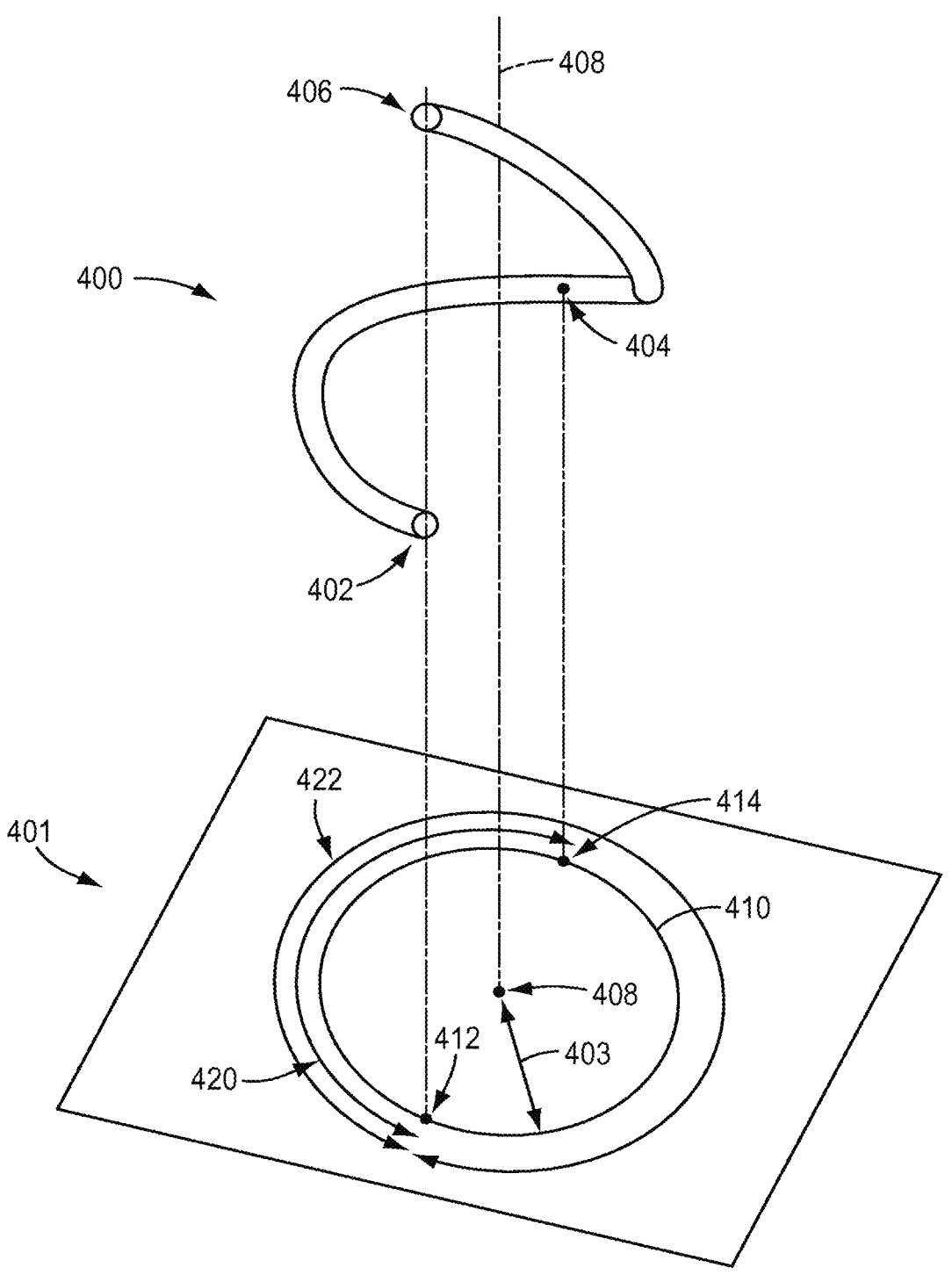
FIG. 6 is a perspective view of an actuation member in a helical shape and projection in a plane of the angular extent of the helical shape, according to an exemplary embodiment.

An angular extent of a helical path of a constraint tendon is further illustrated in the exemplary embodiment of FIG. 6. As shown in FIG. 6, a helically twisted tendon extends in a helix path 400 around a longitudinal axis 408 (at a centerline of the helical path 400) from a first end 402 to a second end 406. To show the angular extent of the helical path 400, the helical path 400 can be projected onto a plane 401 perpendicular to axis 408. The projection is an arc 410 having a radius of curvature 403 corresponding to the radius of curvature of twisted path 400, with points on arc 410 corresponding to locations on helical path 400. For instance, point 412 on arc 410 corresponds to a first end 402 of the helical path and point 414 on arc 410 corresponds to a point 404 approximately halfway along the length of the helical path. Although helical path 400 is depicted in the exemplary embodiment of FIG. 6 as having a substantially continuous radius of curvature 403, helical path 400 (and therefore arc 410) also may include sections having different curvature and may include one or more straight sections, as discussed above. Therefore, when a helical path is discussed in the exemplary embodiments herein, the helical path may have a helical shape with a substantially continuous radius of curvature or the helical path may include sections with differing radii of curvature, including curved sections with differing radii of curvature and/or straight sections.

As shown in FIG. 6, an angular extent 420 between point 412 and point 414 on arc 410, relative to centerline 408 (also be projected onto plane 401), is approximately 180.degree. Thus, when the angular extent of a helical path is discussed in the exemplary embodiments herein, the angular extent can be determined according to angular extent 420 relative to centerline 408, as shown in FIG. 6. Further, because helical path 400 completes a full 360 degree helical twist from first end 402 to second end 406, point 412 on arc 410 corresponds to both first end 402 and second end 406, with the angular extent 422 between first end 402 and second end 406 being 360 degrees. Thus, in the exemplary illustration of FIG. 6, arc 410 forms a complete circle. However, in embodiments in which a helical path does not complete a 360 degree twist, arc 410 will not complete a circle because the angular extent of the helical path is less than 360 degrees.

According to an exemplary embodiment, constraint tendons 330, 332, 334, 336 extend along a helical path so that constraint tendons 330, 332, 334, 336 have an angular extent of approximately 360 degrees along the entire length of wrist 310. For instance, constraint tendons 330, 332, 334, 336 may extend along a helical path having an angular extent of approximately 90 degrees between each disk 311-315 of wrist 310 when wrist 310 includes four disks 311-315. In other words, constraint tendons 330, 332, 334, 336 may be extend along a helical path having an angular extent of approximately 90 degrees each between disk 315 and disk 314, between disk 314 and disk 313, between disk 313 and disk 312, and between disk 312 and disk 311. In another exemplary embodiment, a wrist may include six disks with the constraint tendons of the wrist extending along a twisted path having an angular extent of approximately 60 degrees between each disk of the wrist, with a total angular extent along the entire wrist being 360 degrees for the constraint tendons. Thus, constraint tendons may extend along a twisted path having an angular extent equaling the total angular extent across the wrist for the constraint tendon (e.g., 360 degrees), divided by the number of disks of the wrist, according to an exemplary embodiment. However, various exemplary embodiments of the present disclosure contemplate the constraint tendons of a wrist may extend along a helical path to other angular extents. For example, constraint tendons may extend along a helical path such that the amount of angular extent differs between differing disks of a wrist. Such a configuration may provide wrist that achieves differing degrees of bending (articulating) along differing sections along the length of the wrist. Further, the total angular extent of constraint tendons may be an integer multiple of 360 degrees, such as when an instrument includes an integer multiple of wrists, according to an exemplary embodiment. Further constraint tendons may extend along a helical path a different amount than approximately 90 degrees between disks, such as, for example, approximately 180 degrees, according to an exemplary embodiment. According to an exemplary embodiment, the constraint tendons may extend along a helical path in an amount described in the exemplary embodiments of U.S. Provisional Application No. 61/943,084, filed on Feb. 21, 2014, which is hereby incorporated by reference in its entirety.

Figure 7A:
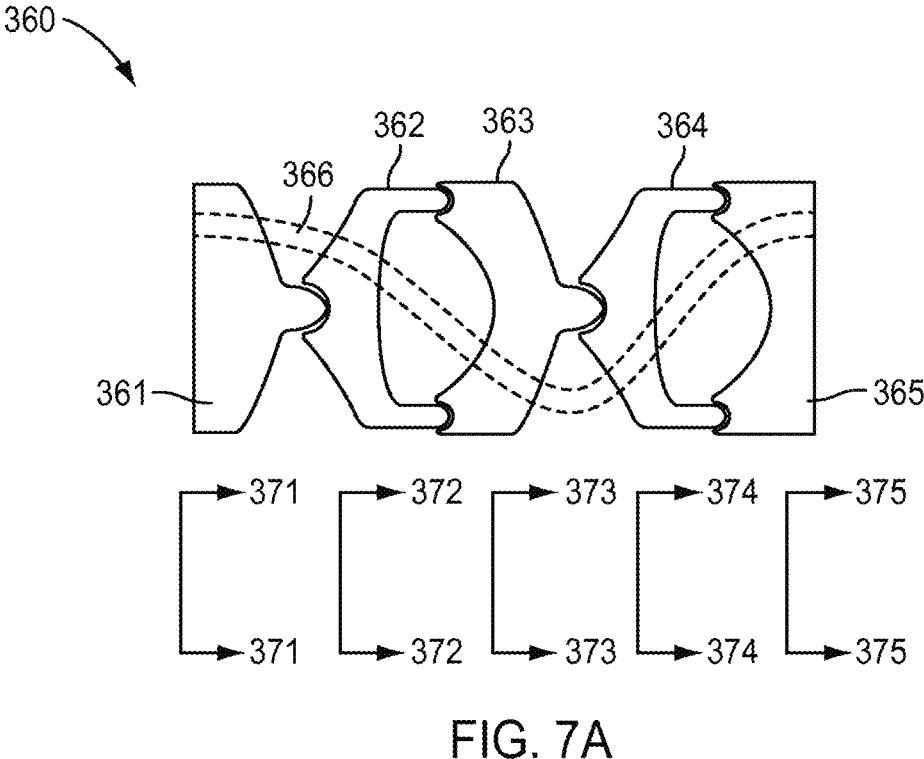
FIGS. 7A and 7B are a side view of an exemplary embodiment of a jointed link structure and cross-sectional views of disks of the jointed link structure to illustrate a helical path of a constraint tendon.
Figure 7B:
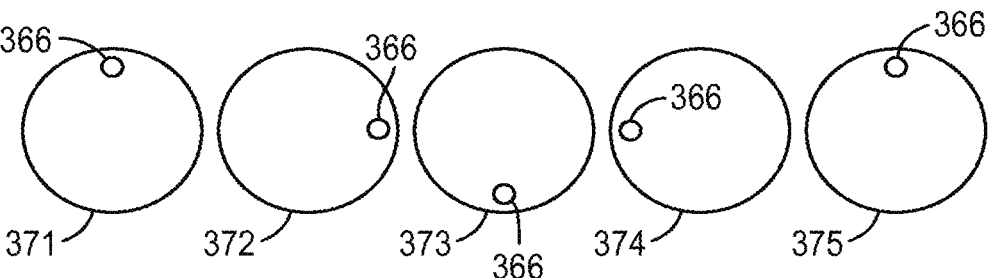

To illustrate the helical path of a constraint tendon, a side view of a wrist 360 including disks 361-365 is shown in the exemplary embodiment of FIG. 7A with the helical path 366 of a single constraint tendon through disks 361-365 shown in dashed lines to facilitate viewing of the helical path, although differing numbers of constraint tendons are contemplated, as discussed in regard to the exemplary embodiment of FIG. 3 above. Further, respective cross-sections 371-375 through disks 361-365, shown in FIG. 7B, illustrate the position of the path 366 of the constraint tendon through disks 361-365. In the exemplary embodiment of FIG. 7A, the path 366 of the constraint tendon follows a helical path having an angular extent of approximately 90 degrees from disk to disk, although other angular extents may be utilized, as discussed above.

Twisting constraint tendons so as to traverse a helical path through at least a portion of a wrist provides advantages other than constraining the motion of the wrist to provide accurate control of the movement and shape of the wrist. For instance, constraint tendons may extend along a helical path so that constraint tendons are positioned in differing locations than joints between disks of a wrist. As shown in the exemplary embodiment of FIG. 3, wrist 310 includes a joint 322 between disks 311 and 312 that permits disks 311 and 312 to rotate (i.e., pivot) relative to one another about axis 350 in direction 351. Constraint tendons 334 and 336 extend between disks 311 and 312 so that constraint tendons 334 and 336 do not physically pass through joint 322. In other words, constraint tendons 334 and 336 are offset from joint 322, as shown in FIG. 3. As a result, joint 322 need not include hollow passages for constraint tendons 334 and 336, permitting joint 322 to be a smaller size while also functioning to bear compressive loads between disks 311 and 312.

Constraint tendons may follow twisted paths to avoid joints connecting disks so the constraint tendons are offset or otherwise adjacent to the joints. For instance, constraint tendons 334 and 336 may extend between disks 311 and 312 on an open side of wrist 310 where an aperture 340 is provided between disks 311 and 312 (when wrist 310 is in the straight or neutral configuration shown in FIG. 3) so that constraint tendons 334 and 336 do not pass through joint 322, which would otherwise lead to weakening of joint 322 due to passages for constraint tendons 334 and 336 through joint 322. According to an exemplary embodiment, joint 322 may include a surface 304 in disk 311 and a surface 306 in disk 312 that contact one another to form a rotating joint between disk 311 and disk 312. Constraint tendons 334 and 336 may extend between disks 311 and 312 such that constraint tendons 334 and 336 do not pass through surfaces 304 and 306, which would otherwise require passages through and weakening of surfaces 304 and 306. For instance, constraint tendons 334 and 336 may be offset from surfaces 304 and 306 of joint 322 in a transverse direction.

Similarly, constraint tendons 330 and 334 may extend between disks 313 and 312 so constraint tendons 330 and 334 do not pass through joint 324, which permit disks 313 and 312 to rotate relative to one another about axis 352 in direction 352; constraint tendons 330 and 332 may extend between disks 314 and 313 so constraint tendons 330 and 332 do not physically pass through joint 326, which permit disks 314 and 314 to rotate relative to one another about axis 354 in direction 355; and constraint tendons 332 and 336 may extend between disks 314 and 315 so constraint tendons 332 and 336 do not physically pass through joint 328, which permit disks 315 and 314 to rotate relative to one another about axis 356 in direction 357.

Figure 8A:
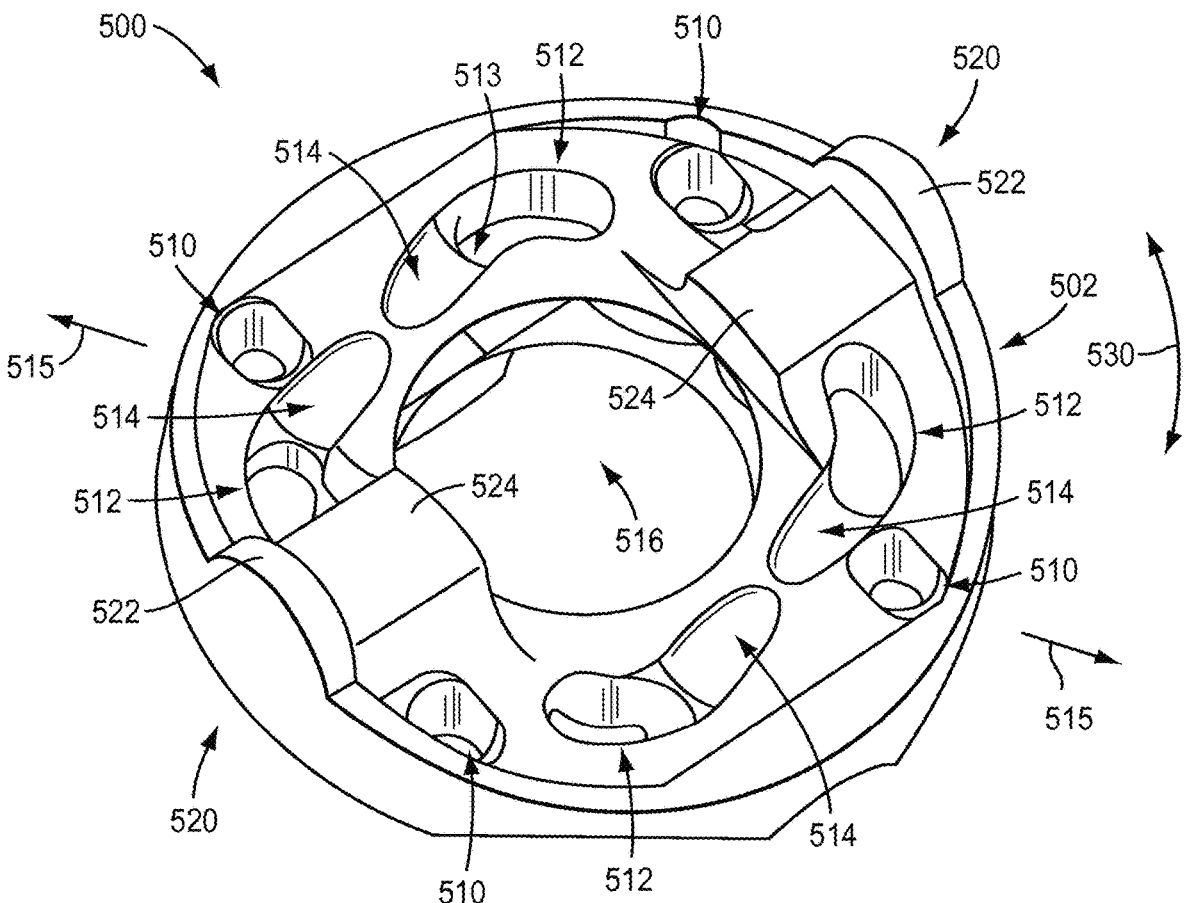
FIG. 8A is a top perspective view of a disk of a jointed link structure, according to an exemplary embodiment.

Disks of a wrist may be configured to locate and/or direct constraint tendons as they pass through the disks. For example, it may be desirable to avoid having the constraint tendons passing through joints between disks. Turning to FIG. 8A, a perspective view is shown of an exemplary embodiment of a disk 500. Disks 311-315 of wrist of FIGS. 3 and 5 may be configured according to disk 500. Disk 500 includes one or more drive tendon apertures 510 through which drive tendons may pass. For instance, when disks 311-315 of the exemplary embodiment of FIGS. 3 and 5 are configured according the exemplary embodiment of disk 500, actuation elements 320 may extend through drive tendon apertures 510. Further, disk 500 may include one or more constraint tendon apertures 512 through which constraint tendons may pass. Thus, when disks 311-315 of wrist 310 are configured according to the exemplary embodiment of disk 500, constraint tendons 330, 332, 334, 336 may extend through constraint tendon apertures 512. Disk 500 may further include a central aperture 516 through which one or more flux conduits (e.g. electrical conductors or optical fibers) or other actuation elements, such as for an end effector, may extend.

Because constraint tendons extend in a helical path along at least a portion of a wrist, constraint tendons may sweep (e.g., move in a direction 530 relative to disk 500) through a larger circumferential extent than drive tendons, which extend in a substantially straight direction between the disks of a wrist, when the wrist is actuated to articulate and bend. Constraint tendon apertures 512 may be located close to an outer periphery 502 of disk 500 because less sweep of constraint tendons may occur when the constraint tendons are positioned further away from a central aperture 516 of disk. Although some sweep of constraint tendons may still occur, locating constraint tendon apertures 512 closer to periphery 502 also provides more space for central aperture 516 and/or joint structures 520 of disk 500. As shown in the exemplary embodiment of FIG. 8A, drive tendon apertures 510 and constraint tendon apertures 512 may both be located close to outer periphery 502 of disk 500 in similar positions along a radial directions 515 relative to central aperture 516.

According to another exemplary embodiment, drive tendon apertures 510 and constraint tendon apertures 512 may be located at different locations along radial directions 515. For example, constraint tendon apertures 512 may be radially offset from drive tendon apertures 510 so that constraint tendon apertures 512 are located along radial directions 515 closer to central aperture 516 than drive tendon apertures 510. As a result, constraint tendons extending through constraint tendon apertures 512 may be located radially inward of joint structures 520 of disk 500 so that the constraint tendons do not interfere with joint structures 520. In another example, constraint tendon apertures 512 for constraint tendons extending along differing helical path directions can be offset from one another. For example, apertures for constraint tendons 330 extending along a helical path in a first direction 342 (such as, for example, in a left-handed direction in a proximal to distal direction) in FIG. 5 and apertures for constraint tendons 334 extending along a helical path in a second direction 344 (such as, for example, in a right-handed direction in the proximal to distal direction) can be offset to minimize or avoid friction between the constraint tendons extending in differing directions.

According to an exemplary embodiment, drive tendon apertures 510 may be located at a distance of, for example, about 0.095 inches to about 0.100 inches from central aperture 516 along radial direction 515 and constraint tendon apertures may be located at a distance of, for example, about 0.080 inches to about 0.085 inches from central aperture 516 along radial direction 515. In an exemplary embodiment in which constraint tendon apertures 512 are radially offset from drive tendon apertures 510, a disk 500 may include four constraint tendon apertures 512, as shown in the exemplary embodiment of FIG. 8A, for a corresponding number of constraint tendons, although other numbers of constraint tendon apertures 512 and constraint tendons may be utilized. For instance, three, five, six, seven, eight, or more constraint tendons apertures 512 and constraint tendons may be used. According to an exemplary embodiment, the number of constraint tendons and constraint tendon apertures 512 used may equal, for example, the number joints in a wrist including disk(s) 500 plus one.

To accommodate the sweep of constraint tendons, constraint tendon apertures 512 may have, for example, a different shape than drive tendon apertures 510. For instance, drive tendon apertures 510 may have a substantially circular transverse cross-section, while constraint tendon apertures 512 may have elongated and non-circular cross-sections, such as being elongated along direction 530. For example, constraint tendon apertures 512 may have an oval, elliptical or kidney shape. In another example, constraint tendon apertures 512 may span along direction 530 to a differing extent than drive tendon apertures 510. For instance, constraint tendon apertures 512 may span to a greater extent along direction 530 than drive tendon apertures 510. According to an exemplary embodiment, drive tendon apertures 510 may have a diameter ranging from, for example, about 0.020 inches to about 0.025 inches and constraint tendon apertures 512 may have a length along circumferential direction 530 of, for example, about 0.020 inches to about 0.025 inches, with drive constraint tendon apertures 512 being equal to or greater in length or diameter than drive tendon apertures 510. Due to the elongated shape and/or circumferential length of constraint tendon apertures 512, constraint tendon apertures 512 may better accommodate the sweep of constraint tendons that extend through constraint tendon apertures 512 as a wrist is actuated to bend from its neutral position.

According to an exemplary embodiment, disk 500 may include a recessed surface portion 514 located adjacent to and extending from a constraint tendon aperture 512. Because constraint tendons extend along helical paths along at least a portion of a wrist, constraint tendons may sweep along circumferential direction 530 and against a circumferential edge 513 of constraint tendon apertures 512. By providing a recess surface portion 514 adjacent to constraint tendon aperture 512, the sweep of a constraint tendon may be further accommodated, such as by permitting the constraint tendon to enter into recess surface portion 514 when the constraint tendon sweeps against a circumferential edge 513 of a constraint tendon aperture 512. Recess surface portion 514 may have, for example, an elongated shape with a depth that is substantially constant or a depth that varies, such as, for example, by decreasing in a direction away from a constraint tendon aperture that the recess surface portion 514 is adjacent to. The latter therefore providing a ramp-like feature from aperture 512 up to the surface of disk 500. According to an exemplary embodiment, recess surface portions 514 may slope at an angle, for example, ranging from about 20 degrees to about 30 degrees.

According to an exemplary embodiment, disk 500 may include joint structures 520 to form joints between adjacent disks. Joint structures 520 may be configured in various ways. For example, joint structures 520 may include cycloidal shapes, as described in U.S. Pat. No. 8,887,595, published Nov. 18, 2014, which is hereby incorporated by reference in its entirety or may be configured according to the exemplary embodiments of U.S. Pat. No. 8,911,428, published Dec. 16, 2014, which is hereby incorporated by reference in its entirety. Joints 322, 324, 326, 328 of the exemplary embodiment of FIG. 3 may be configured like joint structures 520. According to an exemplary embodiment, a joint structure 520 may include a projection 522 (or tooth). Projection 522 may be inserted in a corresponding recess of an adjacent disk, such as disk 540 shown in the exemplary embodiment of FIG. 8B, which may include a recess 552 having a corresponding shape and configured to receive projection 522 of disk 500. According to an exemplary embodiment, recess 552 may form one or more pins to intermesh with projection 522. Thus, in a pair of adjacent disks, a first disk may include one or more projections (or teeth) and a second disk may include one more recesses (or pins) configured to receive the projection(s).

Figure 8B:
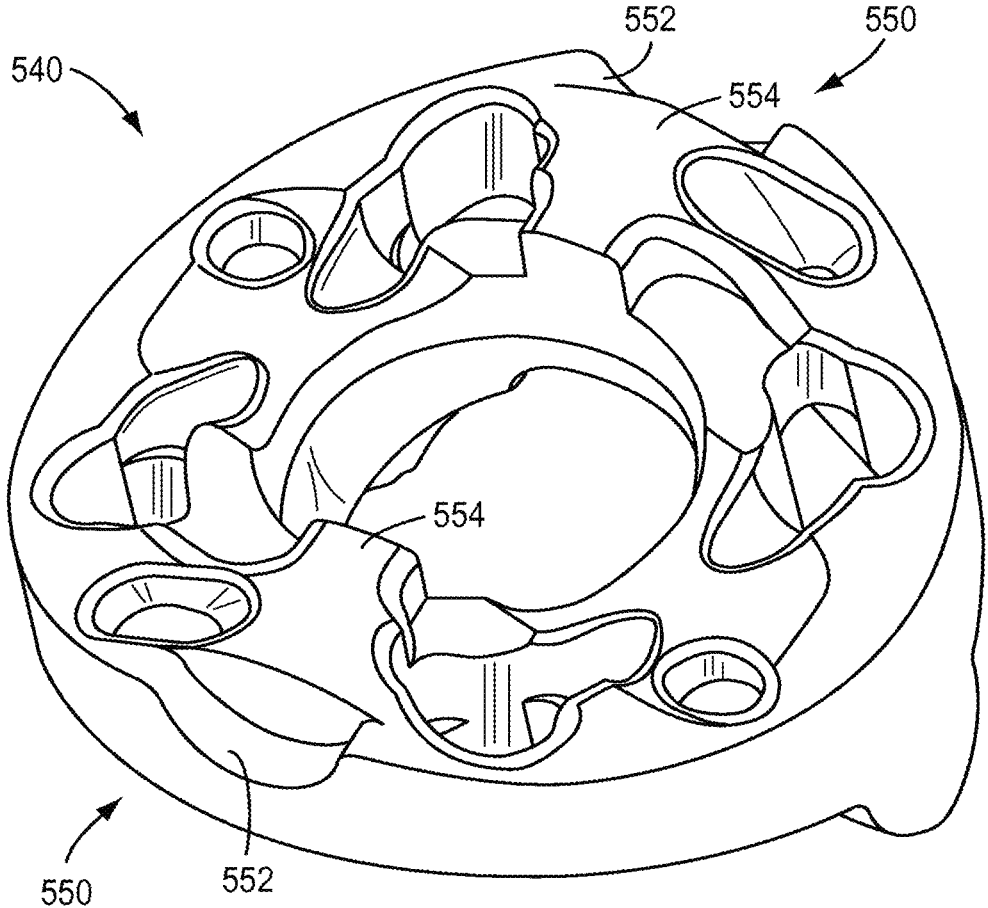
FIG. 8B is a top perspective view of a disk of a jointed link structure, according to an exemplary embodiment.

According to an exemplary embodiment, a joint structure 520 of disk 500 of the exemplary embodiment of FIG. 8A may further include a projection 524 configured to contact a corresponding projection of an adjacent disk, such as projection 554 of disk 540 in the exemplary embodiment of FIG. 8B. As a result, projection 524 may serve as a compression load bearing surface between adjacent disks. Because constraint cables are located separately from and directed away from joint structures 520, including load bearing projections 524, joint structures 520 are not weakened by constraint cable apertures extending through joint structures 520. Thus, joint structures 520, including load bearing projections 524 may be made larger, which increases the loads that may be accommodated by a wrist including disks like disk 500, making the wrist stronger.

Another advantage provided by extending constraint tendons along helical paths is the substantial conservation of lengths of constraint tendons when a wrist is actuated to articulate (e.g., bend). When disks 313, 314 are actuated to pivot relative to one another about axis 354 in direction 355 in FIG. 3, constraint tendons 330 and 332 may change in length between disks 313 and 314. For example, constraint tendons 330 and 332 may experience a positive change in length between disks 313 and 314 when disks 313 and 314 are rotated relative to one another about axis 354 in a direction away from the side of wrist 310 that constraint tendons 330 and 332 are on between disks 313 and 314. Conversely, constraint tendons 330 and 332 may experience a negative change in length between disks 313 and 314 when disks 313 and 314 are rotated relative to one another about axis 354 in a direction toward the side of wrist 310 that constraint tendons 330 and 332 are on between disks 313 and 314. Other constraint tendons experience similar positive or negative changes in length between other disks when wrist 310 is actuated. Changes in length of constraint tendons may affect the function of constraint tendons to constrain the motion of wrist 310, such as by introducing slack in constraint tendons.

A twisting path for a constraint tendon through an articulatable member, such as a wrist, may be selected to address changes in length of constraint tendons. According to an exemplary embodiment, passive constraint tendons may extend along a helical path along at least a portion of a wrist to substantially conserve the length of the constraint tendons over the entire length of the wrist. A constraint tendon may passively constrain movement of an articulatable member without the use of an actuator, such as a force transmission mechanism and control algorithms controlling the same. For example, in various exemplary embodiments, the movement of disks of a jointed link structure may be passively constrained by constraint members that are not actuatable by an external drive or transmission mechanism. To achieve this, a passive constraint tendon may extend along a helical path so that when an articulated member including the constraint tendon is bent, such as in a pitch and/or yaw motion, the constraint tendon experiences a positive or negative change in length between a first pair of adjacent disks and experiences a corresponding, and opposite, negative or positive change in length between a second pair of adjacent disks that substantially cancels the change in length from the first pair of adjacent disks. As a result, the length of the constraint tendon is substantially conserved. Further, because ends of the constraint tendon are fixed at opposite ends of the articulatable member, which fixes the length of the constraint tendon, the bending motion (e.g., a pitch and/or yaw motion) is permitted because the bending motion does not substantially result in a change in length of the constraint tendon. In contrast, a translation motion, such as to laterally move a wrist into an S-shape, may be substantially prevented because the translation motion does not result in a conservation of the length of the constraint tendon but the fixed ends of the constraint tendon substantially prevent a change in length of the constraint tendon.

Turning to the exemplary embodiment of FIG. 5, constraint tendons 332 and 336 experience a negative change in length when disks 315 and 314 are rotated about axis 356 in direction 357 toward each other on the side of wrist 310 that constraint tendons 332 and 336 are located. Constraint tendons 332 and 336 extend along a helical path through wrist 310 so that constraint tendons 332 and 336 extend between disks 313 and 312 on an opposite side of wrist 310 from where constraint tendons 332 and 336 extend between disks 315 and 314. Thus, when disks 313 and 312 are rotated about axis 352 along direction 353 in substantially the same way as disks 315 and 314, constraint tendons 332 and 336 experience a positive change in length between disks 313 and 312 in an amount that substantially cancels the negative change in length between disks 315 and 314, thereby substantially conserving the length of constraint tendons 332 and 336. Similarly, when wrist 310 is actuated in the opposite direction so that constraint tendons 332 and 336 experience a positive change in length between disks 315 and 314 and a negative change in length between disks 313 and 312, the lengths of constraint tendons 332 and 336 are still substantially conserved. Constraint tendons 330 and 334 also may extend along a helical path so that changes in length of constraint tendons 330 and 334 between disks 315 and 314 substantially cancel changes in length of constraint tendons 330 and 334 between disks 313 and 312. In addition, constraint tendons 330, 332, 334, 336 extend along a helical path so that change in length of constraint tendons 330, 332, 334, 336 between disks 314 and 313 substantially cancel changes in length constraint tendons 330, 332, 334, 336 between disks 312 and 311.

According to an exemplary embodiment, when the bend axes 350, 352, 354, 356 of wrist 310 alternate in different (e.g., orthogonal) directions, as shown in FIG. 3, constraint tendons 332 and 336 may extend in a helical path over an angular extent of approximately 180 degrees from the position of constraint tendons 332 and 336 at a location between disks 315 and 314, such as, for example, at location 370 shown in FIG. 3, to the position of constraint tendons 332 and 336 at a location between disks 313 and 312, such as, for example, at location 372 shown in FIG. 3. In this way, constraint tendons 332 and 336 are located on opposite sides of wrist 310 to facilitate conservation of the lengths of constraint tendons 332 and 336. As noted above, constraint tendons 330, 332, 334, 336 may extend in a helical path over an angular extent of approximately 90 degrees from disk 311 to disk 312, from disk 312 to disk 313, and so on, thus providing a helical path having an overall angular extent of approximately 180 degrees from disk 311 to disk 313. Similarly, constraint tendons 330 and 334 may extend along a helical path having an angular extent of approximately 180 degrees from the position of constraint tendons 330 and 334 at a location between disks 315 and 314 to the position of constraint tendons 330 and 334 at a location between disks 313 and 312. In addition, constraint tendons 330, 332, 334, 336 may extend along a helical path having an angular extent of approximately 180 degrees from the position of constraint tendons 330, 332, 334, 336 at a location between disks 313 and 314 to the position of constraint tendons 330, 332, 334, 336 at a location between disks 312 and 311.

According to an exemplary embodiment, by fixing constraint tendons 330, 332, 334, 336 at opposite ends of wrist 310, bend angles of similar joints of wrist will be substantially the same. By providing a wrist that has substantially the same bend angles for similar joints, motions of the wrist may be more easily controlled and may be smoother. According to an exemplary embodiment, when wrist 310 is actuated to bend toward the side of wrist 310 where constraint tendons 332, 336 extend between disks 315 and 314, disks 315 and 314 rotate relative to one another about axis 356 to substantially the same degree that disks 313 and 312 rotate relative to one another about axis 352. This is because axes 356 and 352 are substantially parallel to one another. Similarly, when wrist 310 is actuated to cause rotation between disks 311 and 312 about axis 350, disks 313 and 314 also rotate about axis 354 to substantially the same degree.

According to an exemplary embodiment, all of the constraint tendons of a wrist may extend in helical paths in the same circumferential direction from a distal disk (e.g., disk 311) to a proximal disk (e.g., disk 315). However, in such an exemplary embodiment, one or more of the constraint tendons may pass through one or more joint structures between adjacent disks, which may result in weakening of the joint structure(s). To address this, constraint tendons can be routed to extend along helical paths in different directions. For instance, one constraint tendon may extend along a twisted path in a right-handed or left-handed direction along the proximal-distal direction of an instrument and another constraint tendon may extend along a twisted path in the other of the left-handed or right-handed direction along the proximal-distal direction of the instrument. As shown in the exemplary embodiment of FIG. 5, constraint tendon 330 extends along a helical path in a first direction 342 (such as, for example, in a left-handed direction in a proximal to distal direction) and constraint tendon 334 extends along a helical path in a second direction 344 (such as, for example, in a right-handed direction in the proximal to distal direction) differing from first direction 344 from disk 311 to disk 315. For instance, first direction 342 and second direction 344 are in directions opposite to one another. By extending constraint tendons 330 and 334 along helical paths in respective directions 342 and 344 from disk 311 to disk 315, constraint tendons 330 and 334 can extend between disks 311-315 without passing through any of joints 322, 324, 326, 328.

Similarly, constraint tendons 332 and 336 extend along helical paths in respective opposite directions 344 and 342 from disk 311 to disk 315 so that constraint tendons 332 and 336 do not physically pass through any of joints 322, 324, 326, 328. According to an exemplary embodiment, at least a portion of both constraint tendons 330 and 336 extend along helical paths in direction 342 from disk 311 to disk 315. According to an exemplary embodiment, at least a portion of both of constraint tendons 334 and 332 extend along helical paths in direction 344 from disk 311 to disk 315. In other words, when wrist 310 includes four constraint tendons 330, 332, 334, 336, two of the constraint tendons may extend along a helical path along direction 342 from disk 311 to disk 315 and the other two constraint tendons may extend along a helical path in direction 344 from disk 311 to disk 315.

One consideration in configuring constraint tendons is the amount of friction between the constraint tendons and components of a wrist, which can impact motion of the wrist, power needed to actuate the wrist, and/or wear on the wrist components. For instance, in wrists that use multiple sets of actuation members to actively constrain a wrist, the actuation members typically extend along a straight path through the instrument and wrist, with bending occurring as the wrist bends. In light of the increased amount of friction that can result between constraint tendons and wrist components due to a helical path of constraint tendons as compared to, for example, a straight path, constraint tendons may extend along helical paths in a way to help minimize friction.

According to an exemplary embodiment, extending constraint tendons 330, 332, 334, 336 along helical paths to have an angular extent of approximately 90 degrees as the tendons traverse between each pair of disks 311-315 does not result in a significant increase in friction in comparison to conventional wrists that utilize multiple sets of straight tendons to constrain joint motion. This is because although constraint tendons 330, 332, 334, 336 extend along helical paths, a wrap angle, which can be used to determine the amount of friction between constraint tendons 330, 332, 334, 336 and wrist components, is not significantly greater than a wrap angle for straight tendons used to constrain joint motion in conventional wrists. Friction between a tendon and its supporting surface(s) may be represented by the capstan equation, $T_{load} = T_{hold} e^{\mu \phi}$, in which $T_{hold}$ is tension applied to the tendon (such as a preloaded tension), $\mu$ is the coefficient of friction between the tendon and support surface(s), $\phi$ is the total angle swept by the twist of the tendon, and $T_{load}$ is the force between the tendon and supporting surface(s). Twisting a tendon through a large angle of $\phi$ thus results in a large $T_{load}$ force between the tendon and the support surface(s). In an exemplary embodiment, using a helical path having an angular extent of approximately 90 degrees between each of neighboring disks 311-315 may provide a wrap angle having, for example, an angular extent of approximately 40 degrees to approximately 70 degrees at, for example, three bend locations 345, 346, 347 shown in the exemplary embodiment of FIG. 5.

The various wrist exemplary embodiments described herein may include disks arranged in various configurations. For example, the configuration shown in the exemplary embodiment of FIG. 3 may be referred to as an "ABAB" wrist due to the alternating orthogonal directions of axes

350, 352, 354, 356. In other exemplary embodiments, a wrist can utilize a configuration in which axes of rotation between disks do not alternate in orthogonal directions but instead follow an "ABBA" configuration so that two consecutive axes (e.g., axes of middle disks) extend in substantially the same direction and are "bookended" by axes that extend in the same direction but are orthogonal to the two consecutive axes.

An ABBA configuration acts similarly to a constant velocity joint, which may be desirable when rolling motions are transmitted through the wrist. For instance, when a wrist is used in an instrument and a rolling motion is input to the instrument shaft, the rolling motion is transmitted through the wrist, causing a distal end of the instrument, which may include an end effector, to roll as well. Because a wrist includes one or more joints, the wrist acts like an input and output shaft of a vehicle drive train connected via one or more joints. As one of ordinary skill in the art is familiar with, when an angle exists between the input and output shaft of a vehicle drive train, a variation in speed occurs between the input shaft and output shaft, which is undesirable. A wrist with an ABBA mechanism addresses this consideration by acting like a constant velocity joint, similar to a double Cardan joint, with the two A joints having substantially the same angle and the two B joints having substantially the same angle, thereby resulting in a substantial cancellation of speed variation between the input and output sides. Thus, an ABBA wrist can minimize or eliminate a variation in speed between an input and output side of the wrist for rolling motions applied to an instrument shaft.

Although an ABBA configuration minimizes or eliminates variation in speed between an input and output side of a wrist for rolling motion, an ABAB configuration, such as the exemplary embodiment of FIG. 3, may be used to advantageously provide a wrist 310 in which constraint tendons 330, 332, 334, 336 extend along helical paths a minimal amount per disk 311-315, in comparison to an ABBA configuration, while also substantially conserving the lengths of constraint tendons 330, 332, 334, 336 and positioning constraint tendons 330, 332, 334, 336 so that constraint tendons 330, 332, 334, 336 do not pass through joints connecting disks. As a result, precise control of movement of the wrist 310 may be obtained with smooth motions and joints connecting disks 311-315 may be small.

Although a wrist mechanism with an ABAB configuration provides a disadvantage of naturally providing a speed variation between its input and output side, extending constraint tendons along helical paths through at least a portion of a wrist and fixing the constraint tendons at opposite ends of the wrist provide significant advantages that at least offset this disadvantage. Further, any speed variation may be compensated for by control systems that regulate input rotational speed to the wrist to accomplish rolling, such as by varying an input speed according to a bend angle of the wrist to compensate for variation in speed.

Figure 9:
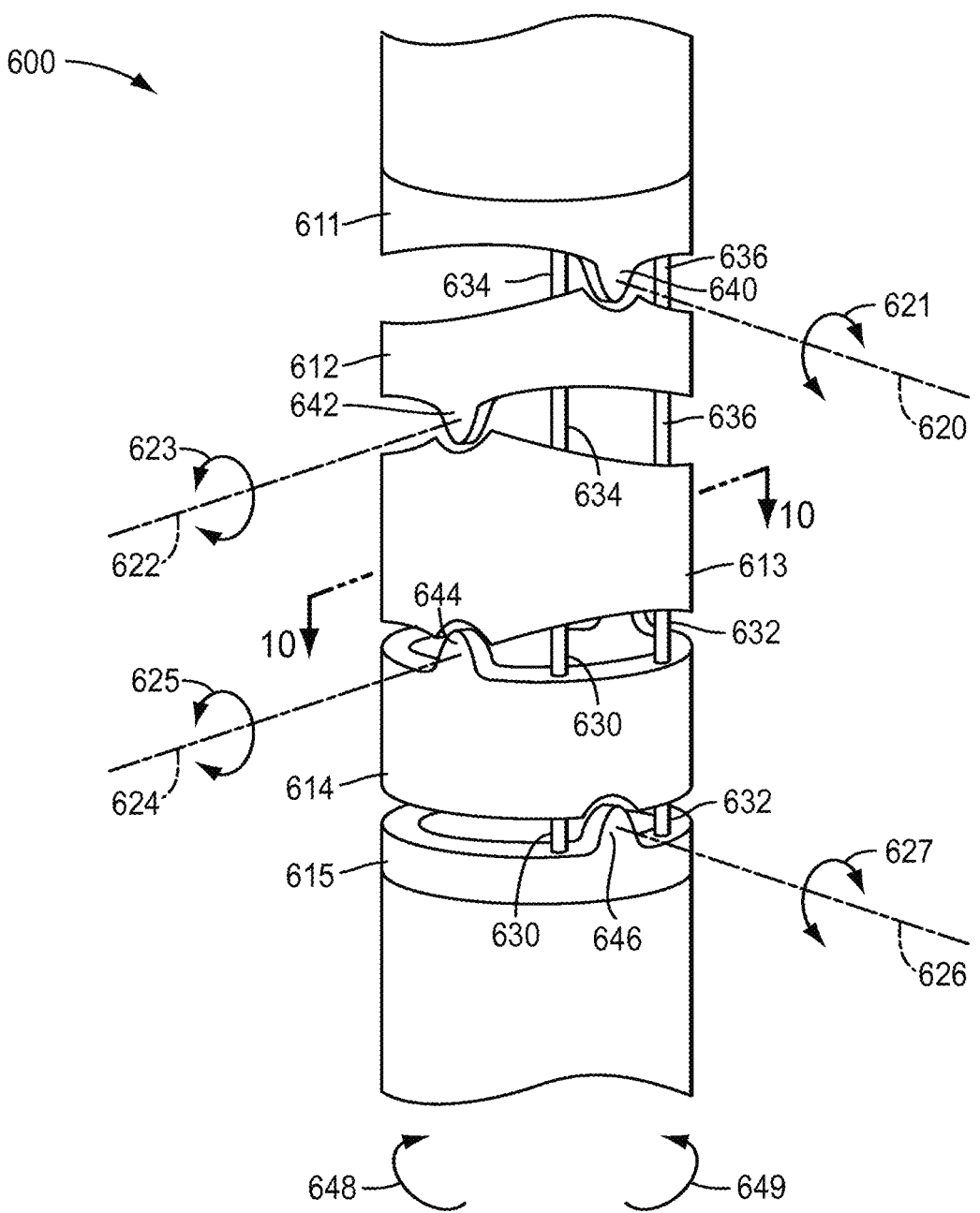
FIG. 9 is a partial view of a distal portion of a surgical instrument including a jointed link structure, according to an exemplary embodiment.

Turning to FIG. 9, one exemplary embodiment of an ABBA wrist that utilizes constraint tendons is depicted. In FIG. 9, wrist 600 includes disks 611-615 arranged in an ABBA joint configuration. In particular, a joint 640 between disks 611 and 612 can permit rotation of disks 611 and 612 about axis 620 in direction 621, a joint 642 between disks 612 and 613 can permit rotation of disks 612 and 613 about axis 622 in direction 623, a connection 644 between disks 613 and 614 can permit rotation of disks 613 and 614 about axis 624 in direction 625, and a connection 646 between disks 614 and 615 can permit rotation of disks 614 and 615 about axis 626 in direction 627. As shown in the exemplary embodiment of FIG. 9, axes 620 and 626 may extend in substantially the same direction, axes 622 and 624 may extend in substantially the same direction, and axes 620 and 626 may be substantially orthogonal to axes 622 and 624, thereby creating the ABBA joint axis configuration (or arbitrary pitch-yaw-yaw-pitch rotation of the disk pairs).

Wrist 600 further includes constraint tendons fixed at opposite ends of wrist 600. As shown in the exemplary embodiment of FIG. 9, wrist 600 includes four constraint tendons 630, 632, 634, 636, although other numbers of constraint tendons may be used. Unlike the exemplary embodiment of FIG. 3, in which constraint tendons extend along a helical path having an angular extent of approximately 90 degrees between each pair of disks, in the exemplary embodiment of FIG. 9, constraint tendons 630, 632, 634, 636 are substantially straight from disk 611 to 612, from disk 612 to disk 613, from disk 613 to disk 614, and from disk 614 to disk 615, but extend along a helical path having an angular extent of approximately 180 degrees across disk 613, such as, for example, along a twisted path or another path across disk 613 to reach a point 180 degrees away. As a result, the lengths of constraint tendons 630, 632, 634, 636 may be conserved when wrist 600 is articulated (e.g., bent). In other words, instead of extending along a helical path with an angular extent of approximately 90 degrees for all joints, constraint tendons in an ABBA configuration would have extend along a helical path with an angular extent of approximately 180 degrees between the B type joints and a helical path with an angular extent of approximately 0 degrees across the A type joints.

Figure 10:
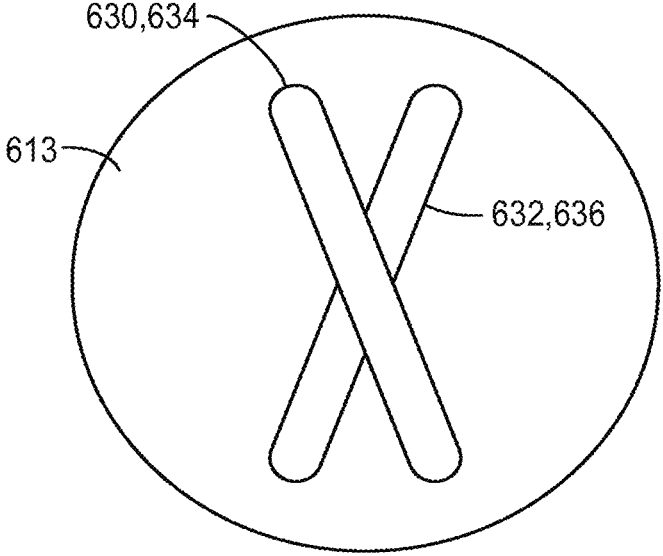
FIG. 10 is a cross-sectional view along line 10-10 in FIG. 9.

This is further illustrated in FIG. 10, which is a cross-sectional view along lines 10-10 in FIG. 9. As shown in FIG. 10, each of constraint tendons 630 and 632 may traverse an angular extent of approximately 180 degrees across disk 613. Constraint tendons 634 and 636 would have the same angular extent as constraint tendons 630 and 632 although entering and exiting disk 613 at different locations. Because constraint tendons 630, 634 and constraint tendons 632, 636 respectively cross over one another, constraint tendons 630, 634 and constraint tendons 632, 636 are depicted in the same location in the cross-sectional view of the exemplary embodiment of FIG. 10. Thus, although the ABBA configuration could minimize speed variation between its input and output sides for rotation (roll) motion, the constraint tendons may pass through the center of the wrist. Although wrist 600 may be configured so constraint tendons 630, 632, 634, 636 are helically twisted along paths extending along a periphery of disk 613, such a design may be less practical than extending the paths across the center of disk 613.

For instance, when wrist 600 uses the disks 500 and 540 of the exemplary embodiment of FIGS. 8A and 8B, constraint tendons would pass through a central lumen provided by central aperture 516 of disks, thus potentially interfering with any actuation members that may otherwise pass through the central lumen. Thus, if the central lumen would otherwise receive an actuation member for an end effector, the end effector actuation member would have to be routed through a different lumen and may need a different design when not located in the central lumen. Further, because the angular extent of the helical path of constraint tendons 630, 632, 634, 636 is greater, the wrap angle for constraint tendons 630, 632, 634, 636 is also greater, which results in a larger amount of friction between constraint tendons 630, 632, 634, 636 in comparison to a wrist with an ABAB configuration. A wrist 600 with an ABAB configuration may be used in, for example, relatively large diameter instruments subjected to relatively small loads. According to another exemplary embodiment, constraint tendons 630, 632, 634, 636 may be configured to extend along paths that do not pass through the center of a central lumen. However, such an embodiment would result in a larger wrap angle for constraint tendons 630, 632, 634, 636, which can lead to increased friction between constraint tendons 630, 632, 634, 636 and disk 613.

Although the exemplary embodiments of FIGS. 3 and 9 depict wrists including four joints, the wrists and other jointed link structures articulatable members according to the exemplary embodiments described herein are not limited to four joints. For example, a wrist and other articulatable members may have two disks, three disks, five joints, six joints, eight joints, or a greater number of joints.

As discussed above with regard to the exemplary embodiments of FIGS. 3, 4, 9, and 10, a jointed link structure, such as a wrist, may include a series of connected disks with tendons to provide a structure for constraining the motion of the wrist. However, other articulatable members, used as wrists or otherwise, in accordance with the various exemplary embodiments of the present disclosure can include other structures. Turning to FIG. 11, an exemplary embodiment of an articulatable member 700 is shown in which a braided structure 710 replaces the disks and forms the main body of the articulatable member 700. As in other exemplary embodiments described herein, the articulatable member 700 can be a wrist, part of a parallel motion mechanism, or other articulatable component of an instrument, such as a surgical instrument. FIG. 11 shows articulable member 700 in a straight (i.e., non-bent) configuration.

According to an exemplary embodiment, the braided structure 710 may have a hollow cylindrical or tubular shape defining a central passage for instrument components. FIG. 12 shows an enlarged view of portion FIG. 12 of braided structure 710 in FIG. 11. As shown, braided structure 710 may include plaits 712 interwoven with one another. In braided structure 710, each of plaits 712 form a helical shaped structure about a centerline of the braided structure 710 extending between the proximal end 702 and the distal end 704 of articulable member 700, the centerline defining a helical axis. In one aspect (not shown), each of plaits 712 make one revolution about the helical axis in the distance between disk 721 and disk 722.

It should be understood that FIG. 11 and enlarged view FIG. 12 are side view depictions of the articulable member 700 including braided structure 710. FIG. 12 shows an enlarged view of a portion of braided structure 710, and more specifically, shows the geometric relationship of the interwoven plaits 712. The warp 711 and weft 713 directions are an attempt to express in two dimensions the helix angles of the plaits 712. The portion of braided structure 710 shown in FIG. 12 is a small, approximately flat section of plaits 712 interwoven with one another. The warp 711 and weft 713 directions shown in FIG. 12 show the approximate angles of the plaits relative to an imaginary axial line extending along the length of the instrument on the outside surface of braided structure 710 (i.e., the line formed by contacting a tangent plane with the curved outer surface of braided structure 710, with the tangent plane being substantially parallel to the centerline of braided structure 710). In one aspect, the angle between the warp 711 direction and the imaginary axial line is the same as to the angle between the weft 713 direction and the imaginary axial line. Stated another way, the helix angle of the plaits 712 aligned with the warp 711 direction is the same as the helix angle of the plaits 712 aligned with the weft 713 direction, the two groups of plaits differing only in handedness of their helical shapes (e.g., one direction of plaits 712 being along a right-handed helical direction and another direction for plaits 712 being along a left-handed helical direction). Such a plait configuration may produce a braided structure 710 with substantially symmetrical bending stiffness about the centerline of the braided structure 710.

Each plait 712 may be formed by a plurality of filaments 714 that extend along the warp 711 or weft 713 directions. Plaits 712 may have a generally rectangular structure with substantially flat surfaces that form an exterior surface 708 of braided structure 710, as shown in FIGS. 11 and 12. However, plaits may have other shapes, such as a circular cross-section, oval cross-section, or other shapes. Filaments 714 may be, for example, monofilaments of nylon or other flexible and strong material and may have a diameter ranging from, for example, about 0.008 inches to about 0.012 inches, such as, for example, about 0.010 inches. Filaments 714 may be made of a material that permits filaments 714 to be flexible, so braided structure 710 may bend when a wrist including braided structure is actuated, but also have a sufficient bending stiffness to minimize or prevent buckling when compressive loads are applied to filaments 714.

Braided structure 710 may be used to constrain the motion of articulatable member 700, as discussed herein, by fixing the ends of braided structure 710. Thus, braided structure 710 may constrain motion of articulatable member 700 instead of using constraint tendons to so, as in the exemplary embodiments of FIGS. 3 and 9. According to an exemplary embodiment, a proximal end 702 of braided structure 710 is fixed to a disk 721, which may in turn connect wrist 700 to other instrument components, such as a distal end of a surgical instrument shaft, a distal end of a parallel motion mechanism, or other instrument structure (not shown). Similarly, a distal end 704 of braided structure 710 is fixed to a disk 722, which may in turn connect articulatable member 700 to other instrument components, such as to a proximal end of an end effector (not shown), or other structure. Disks 721, 722 differ from the disks of an articulatable member, such as disks 311-315 of wrist 300 of the exemplary embodiment of FIG. 3, in that disks 721, 722 are not coupled to one another, such as via joints. Thus, disks 721, 722 may, according to an exemplary embodiment, serve as ends of a wrist that may be in turn coupled to other instrument components.

Braided structure 710 can provide relatively smooth motion for articulatable member 700, for example, when used as a wrist, and be relatively inexpensive to manufacture. Further, similar to a wrist structure having an ABBA configuration, braided structure 710 may minimize or eliminate a speed variation between its input and output sides when subject to rotational (roll) motion. Braided structure 710 may be actuated, for example, by applying a force, such as tension or compression, to actuation members 730 (e.g., pull/pull or push/pull actuation members which may be coupled to and actuated by a force transmission mechanism, as described above with regard to the exemplary embodiment of FIG. 4) connected to distal end 704 of braided structure 710, such as to distal disk 722, to cause braided structure 710, and thus articulatable member 700, to be bent along an arc.

Figure 14:
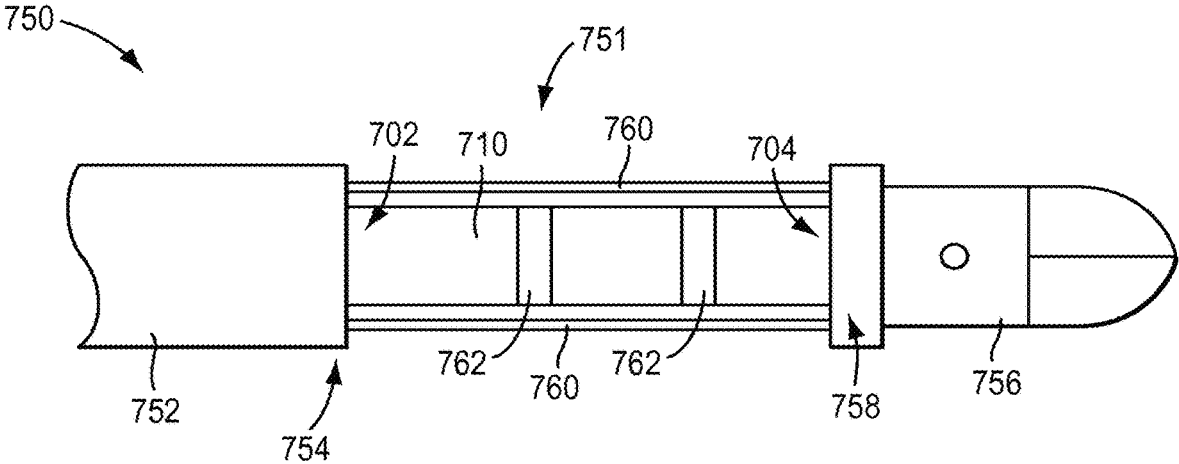
FIG. 14 is a side view of a distal portion of a surgical instrument including a jointed link structure with a braided structure, according to an exemplary embodiment.

According to another exemplary embodiment, the proximal end 702 and distal end 704 of braided structure need not be respectively fixed to disks but instead can be directly fixed to another instrument component without the use of a disk. Turning to FIG. 14, a side view is shown of a distal portion 750 of a surgical instrument that includes a wrist 751 including a braided structure 710 that forms the main body of wrist 751. Braided structure 710 may have the structure and features discussed in regard to the exemplary embodiment of FIG. 11. The proximal end 702 of braided structure 710 is directly fixed to a distal end 754 of a surgical instrument component 572, which may be, for example, a surgical instrument shaft, a distal end of a parallel motion mechanism, or other instrument structure. Further, the distal end 704 of braided structure 710 is directly fixed to a proximal end 758 of an end effector 756, or other structure. Wrist 751 may include actuation members 760 to articulate wrist 751, such as by applying a force, such as tension or compression, to actuation members 751 (e.g., pull/pull or push/pull actuation members), which are in turn connected to proximal end 758 of end effector 756 to cause wrist 751 to be bent along an arc.

Articulatable member 700 may include one or more structures to control the diameter of braided structure 710 so that the diameter of braided structure 710 does not substantially shrink or expand under load, which may otherwise affect the precision of the motion of braided structure 710. As shown in the exemplary embodiment of FIG. 11, one or more disks 720 may be provided around exterior surface 708 of braided structure 710 to control the outer diameter of braided structure (i.e., control the outer diameter in a radial direction). Disks 720 differ from the disks of an articulatable member, such as disks 311-315 of wrist 300 of the exemplary embodiment of FIG. 3, in that disks 721, 722 are not coupled to one another or to disks 721 or 722, such as via joints. As shown in FIG. 11, actuation members 730 may extend through apertures 723 in disks 720 to guide actuation members 730 to distal disk 722. Actuation members 730 may also extend through apertures 725 in disks 721 and 722.

Although two disks 720 are shown in the exemplary embodiment of FIG. 11 to facilitate viewing of braided structure 710, other numbers of disks 720 may be utilized, such as, for example, one, three, four, five, six, or a greater number of disks. Braided structure 710 may further include an internal structure to control the inner diameter of braided structure 710. Turning to FIG. 13, which shows a cross-sectional view of articulatable member 700, an internal structure 740 may be provided inside braided structure 710 to control the inner diameter of braided structure 710. Internal structure 740 may have the shape of a hollow cylinder or tube having a central passage 742 and may be, for example, a spring or hollow tube. Internal structure 740 may be made of metal, plastic, or other material that is strong enough to resist radial deformation of braided structure 710 but also flexible so that internal structure 740 may be elastically deformed when articulatable member 700 and braided structure 710 are actuated and bent.

According to an exemplary embodiment, an articulatable member including a braided structure may use other structures than disks, such as disks 720 of the exemplary embodiment of FIG. 11, to control the diameter of the braided structure. As shown in the exemplary embodiment of FIG. 14, wrist 751 may include bands 762 wrapped around braided structure 710 to control the diameter of braided structure 710. Although two bands 762 are shown in the exemplary embodiment of FIG. 14, other numbers of bands 762 may be utilized, such as, for example, one, three, four, five, six, or a greater number of disks. Further, bands 762 may lack passages for actuation members 760, which extend past bands 762 between proximal end 702 and distal end 704 of braided structure. Thus, as shown in the exemplary embodiment of FIG. 14, wrist 751 with braided structure 710 may lack disks to fix the proximal 702 and distal 704 ends of braided structure 710 and/or disks to control the diameter of braided structure 710.

According to an exemplary embodiment, braided structure 710 may extend along a helical path between its proximal end 702 and distal end 704, such as in direction 706 or in direction 707. For example, the individual filaments 714 may extend along helical paths. Providing a predetermined helical path for braided structure 710 may control the number of DOF's of braided structure 710 and thus control the motion of braided structure 710 and how braided structure 710 constrains the motion of wrist 700. For instance, controlling the helical path traversed by a braided structure 710 may affect the number of degrees of freedom permitted by braided structure 710 due to how individual filaments are positioned relative to bending axes along the length of the braided structure 710.

According to an exemplary embodiment, braided structure 710 may extend along a helical path having an angular extent of approximately 180 degrees between proximal end 702 and distal end 704 to provide braided structure 710 with zero degrees of freedom. For instance, filaments 714 may extend along a helical path having an angular extent of approximately 180 degrees between proximal end 702 and distal end 704. The 180 degree angular extent of the helical path results in a braided structure 710 in which the length of filaments 714 is not conserved when the braided structure 710 is moved. Because ends of the braided structure 710 are fixed and do not permit a change in length, bending and translation motions are substantially prevented, which would otherwise result in a change in length of the braided structure 710. A braided structure 710 with zero degrees of freedom would be resistant to bending like a wrist but may bend a limited degree due to deformation of filaments and/or plaits under load.

According to another exemplary embodiment, braided structure 710 may extend along a helical path having an angular extent of approximately 360 degrees between proximal end 702 and distal end 704 to provide braided structure 710 with two degrees of freedom, such as in arbitrary pitch and yaw directions. For example, filaments 714 may extend along a helical path having an angular extent of approximately 360 degrees as they traverse from the proximal end 702 and to the distal end 704. By extending along a helical path having an angular extent of approximately 360 degrees, braided structure 710 may function like a wrist comprising a series of connected disks in an ABAB configuration with two degrees of freedom, because bending motions in pitch and yaw directions may be permitting because the bending motions are length conservative. Conversely, translation motion, such as to move braided structure 710 into an S-shape, would be substantially prevented because the translation motion would not be length conservative and the fixed ends of the braided structure 710 would substantially prevent a change in length of braided structure 710. On the other hand, because braided structure 710 has only two degrees of freedom when extending along a helical path having an angular extent of approximately 360 degrees, translation motion of braided structure 710 in X-Y space can be constrained, so that braided structure 710 may articulate along an arc (e.g., like a wrist) but one portion of braided structure 710 may not translate laterally relative to another portion of braided structure 710 (e.g., like a parallel motion mechanism, as described below in regard to the exemplary embodiment of FIG. 17 and in U.S. Pat. No. 7,942,868, published May 17, 2011, and U.S. application Ser. No. 11/762,165, filed on Jun. 13, 2007, and published as U.S. Pub. No. US 2008/0065105). A lateral translation movement of one portion of braided structure 710 relative to another portion of braided structure 710 may not be desired for a wrist including the braided structure 710.

According to another exemplary embodiment, braided structure 710 may extend along a helical path having an angular extent of approximately 720 degrees between proximal end 702 and distal end 704, so that the motion of braided structure 710 is substantially unconstrained. For example, filaments 714 may extend along a helical path having an angular extent of approximately 720 degrees as they traverse from the proximal end 702 to the distal end 704. A braided structure extending an angular extent of approximately 720 degrees would be similar to two consecutive braided structures each extending along a helical path having an angular extent of approximately 360 degrees, providing an overall braided structure with 4 DOFs (which would appear to be substantially unconstrained to a user) and permitting both bending movement and translation movement. As a result, not only may braided structure 710 bend in arbitrary pitch and yaw directions like a wrist, but braided structure 710 may move into a S-shape or like a parallel motion mechanism, as described below in regard to the exemplary embodiment of FIG. 17, so that longitudinal axes through each of proximal end 702 and distal end 704 may be offset from one another but still substantially parallel to one another.

When a braided structure 710 is used in an articulatable member 700, braided structure 710 may be used to replace a series of disks connected at joints, as shown in the exemplary embodiment of FIG. 11. In other words, braided structure 710 itself may provide the structure and body of the articulatable member 700 from one end to another. In such an exemplary embodiment, the articulatable member 700 can be used as a wrist and have the same diameters as wrist structures discussed in the exemplary embodiments above. Further, braided structure 710 may have both torsional and compressive stiffness and be placed under both tension and compression.

Figure 15:
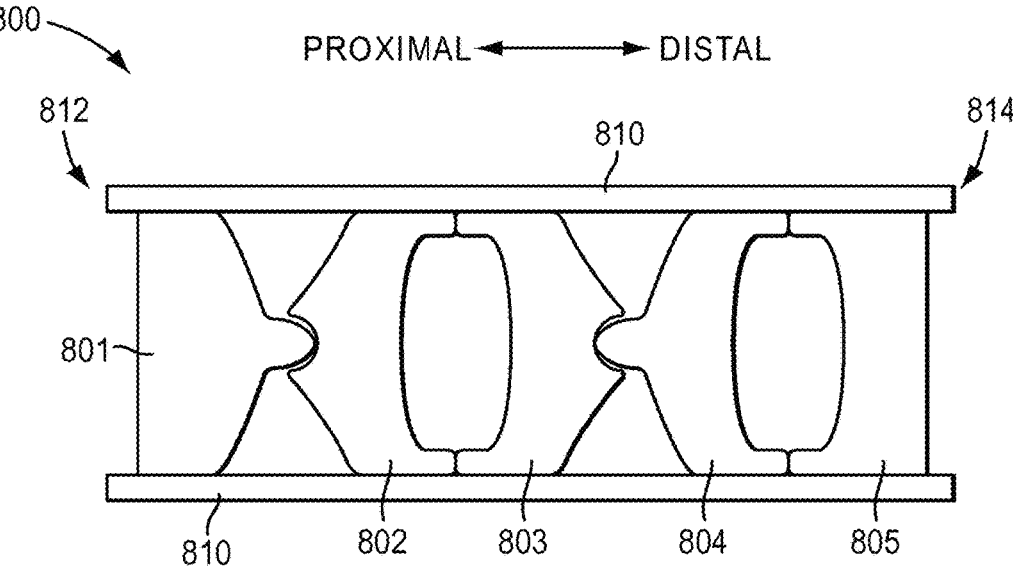
FIG. 15 is a side view of a jointed link structure including a braided structure, according to an exemplary embodiment.

Although braided structure 710 may be used to replace connected disks and to provide wrist with a constrained motion, as in the exemplary embodiment of FIG. 11, a braided structure also may be used in conjunction with connected disks to provide an alternative articulatable member (e.g., wrist) with constrained motion. In this case, the braided structure may replace constraint tendons, such as constraint tendons 330, 332, 334, 336 of the exemplary embodiment of FIG. 3. Turning to FIG. 15, a side view is shown of an articulatable member 800 that includes connected disks 801-805 and a braided structure 810. Disks 801-805 may be connected and configured in the same manner as the exemplary embodiment of FIG. 3 (i.e., in an ABAB configuration and shown in FIG. 15). To constrain motion of disks 801-805, such as to permit controlled bending along an arc a braided structure 810 may be provided about the exterior of disks 801-805, as shown in the exemplary embodiment of FIG. 14. Braided structure 810 may be configured according to the exemplary embodiment of FIG. 11 and include filaments 714 forming interwoven plaits 712 to form an overall hollow cylindrical or tubular structure around disks 801-805. A proximal end 812 and a distal end 814 of braided structure 810 can be fixed relative to disks 801-805. According to an exemplary embodiment, proximal end 812 and distal end 814 of braided structure 810 may be fixed to place braided structure 810 under tension, with disks 801-805 bearing compressive loads. Further, by placing braided structure 810 around an exterior of disks 801-805, an internal diameter of braided structure 810 may be controlled by disks 801-805 themselves, according to an exemplary embodiment.

As discussed in the exemplary embodiments of FIGS. 3-15, an articulatable member with a constrained motion may be a wrist. However, an articulatable member with a constrained motion is not limited to a wrist. According to an exemplary embodiment, an articulatable member with constrained motion may be a parallel motion mechanism, the functions of which are described, for example, in U.S. Pat. No. 7,942,868, published May 17, 2011, and U.S. Pub. No. US 2008/0065105, published Mar. 13, 2008, which are incorporated herein by reference in their entireties.

Figure 16:
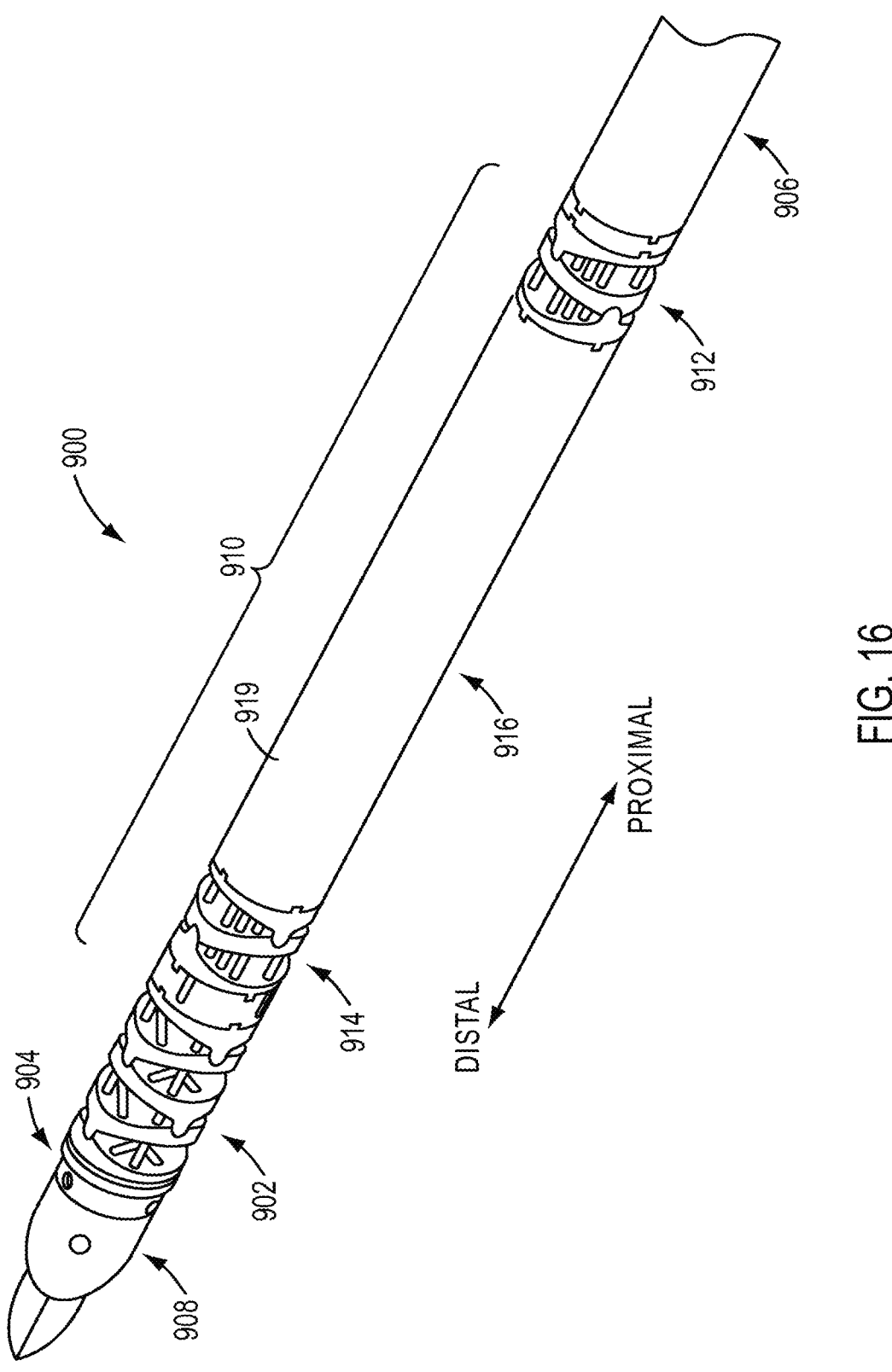
FIG. 16 is a partial perspective view of a distal portion of a surgical instrument including a parallel motion mechanism, according to an exemplary embodiment.

With reference to FIG. 16, a distal portion 900 of a surgical instrument is shown that includes a parallel motion mechanism 910 connected to an instrument shaft 906. The instrument may be a camera instrument or a surgical instrument with an end effector 908 according to the exemplary embodiment of FIG. 2. According to an exemplary embodiment, instrument distal portion 900 may, for example, include a wrist 902, which may be configured according to any of the exemplary embodiments described above, although the instrument may lack a wrist 902.

As shown in the exemplary embodiment of FIG. 16, parallel motion mechanism 910 may include a straight shaft section 916 that separates a proximal joint mechanism 912 from a distal joint mechanism 914. Similar to the exemplary embodiments of U.S. Pat. No. 7,942,868, published May 17, 2011, and U.S. Pub. No. US 2008/0065105, published Mar. 13, 2008, joint mechanisms 912 and 914 and the opposite ends of straight section 916 are coupled together so as to operate in cooperation with each other. According to an exemplary embodiment, proximal joint mechanism 912 and distal joint mechanism 914 may include a plurality of connected disks, similar to a wrist. The disks may include, for example, mechanical stops (not shown) to limit the motion of joint mechanisms 912, 914, such as in pitch and/or yaw directions.

Figure 20:
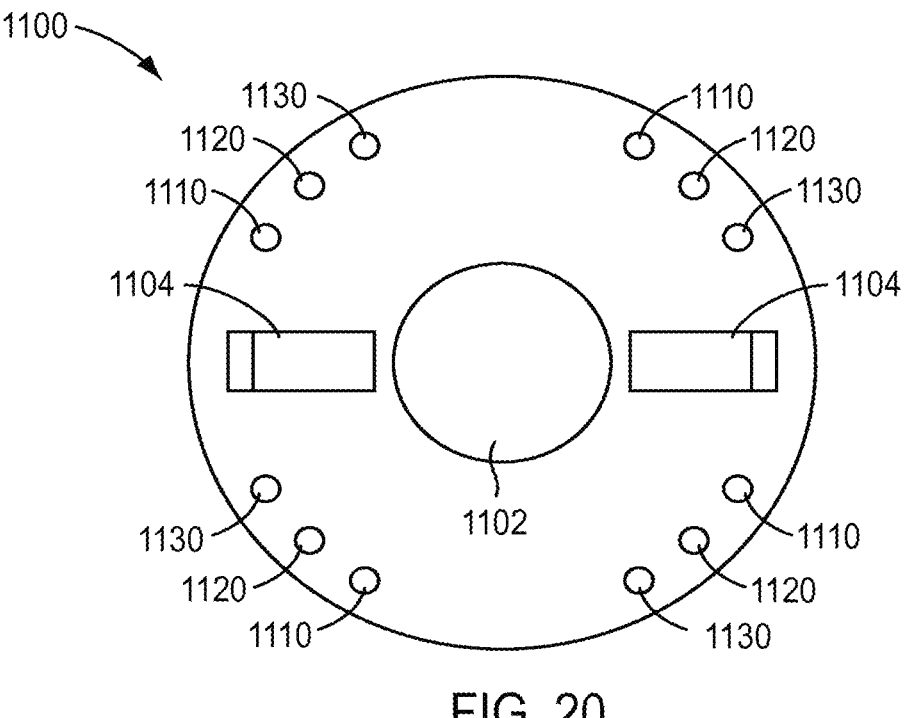
FIG. 20 is an end view of a disk of a parallel motion mechanism, according to an exemplary embodiment.

FIG. 20 shows an end view of an exemplary embodiment for a disk 1100 of a joint mechanism for a parallel motion mechanism. Disk 1100 may include a central aperture 1102, connection portions 1104, and a plurality of apertures for actuation members. For example, disk 1100 may include a plurality of apertures 1110 for wrist drive tendons, a plurality of apertures 1120 for parallel motion mechanism drive tendons, and a plurality of apertures 1130 for constraint tendons, which are discussed further below. As depicted in the exemplary embodiment of FIG. 20, apertures 1110, 1120, 1130 may be located at the same distance (e.g., radius) with respect to a center of disk 1100 (e.g., center of central aperture 1102), or apertures 1110, 1120, 1130 may be located at differing distances (e.g., radius) with respect to the center of disk 1100.

Figure 17:
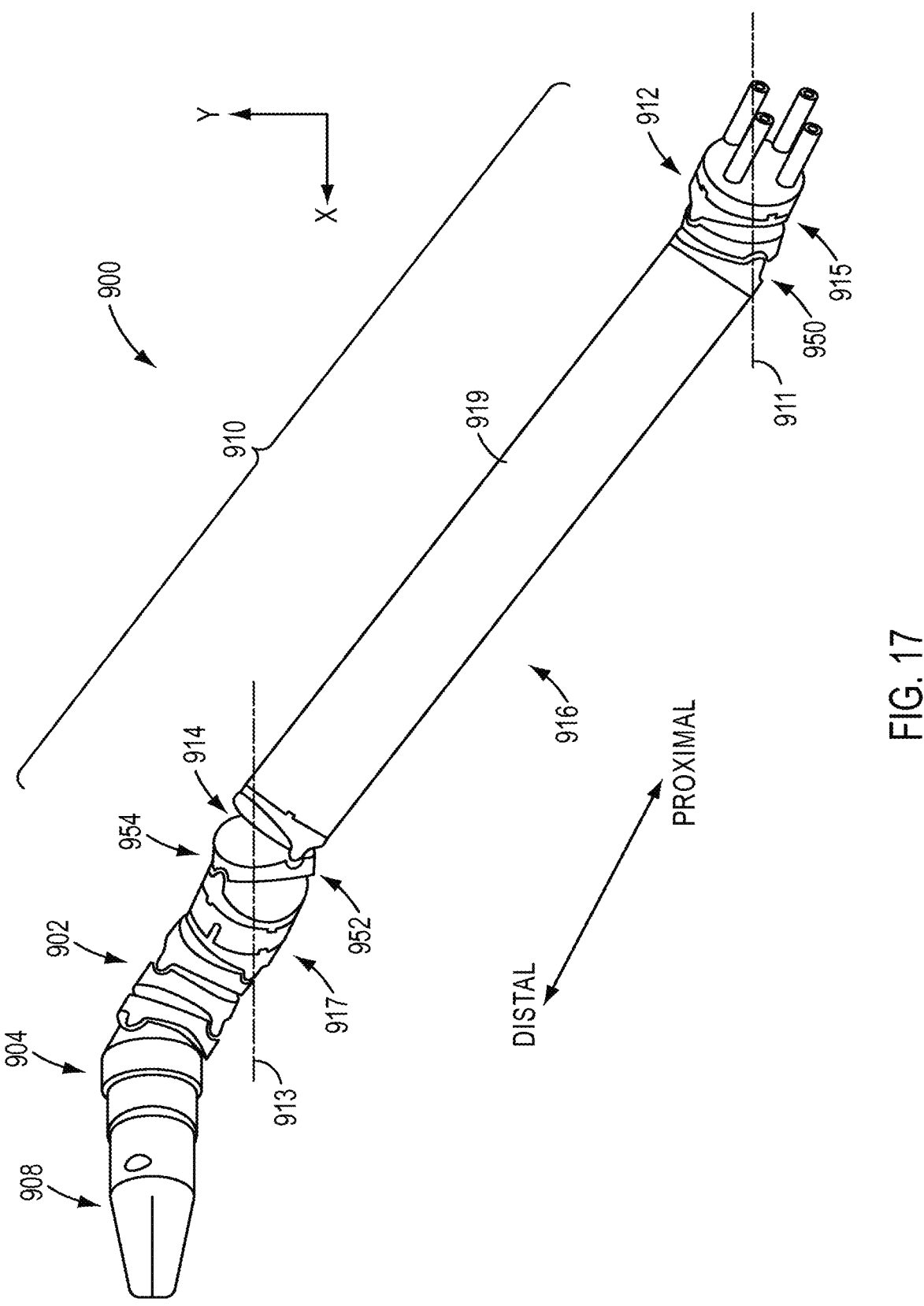
FIG. 17 is a partial perspective view of the distal portion of the surgical instrument of FIG. 16 with the parallel motion mechanism actuated into a deflected configuration, according to an exemplary embodiment.

FIG. 17 shows the exemplary embodiment of FIG. 16 with parallel motion mechanism 910 actuated. As shown in FIG. 16, parallel motion mechanism 910 may control the relative orientations of a distal end portion 917 of parallel motion mechanism 910 and a proximal end portion 915 of parallel motion mechanism 910. As a result, a longitudinal axis 913 through distal end portion 917 of parallel motion mechanism 910 may be substantially parallel to a longitudinal axis 911 passing through proximal end 915 of parallel motion mechanism 910 (longitudinal axis 911 may also be the longitudinal axis of instrument shaft 906, not shown in FIG. 16). Thus, a position of end effector 908, camera device (not shown), or other component at distal end 904 of instrument distal portion 900 may be changed in X-Y space but the orientation of end effector 908 relative to longitudinal axis 911 may be maintained (before any motion due to wrist 902 is accounted for).

Unlike the motion of a wrist, which may be constrained to substantially follow an arc, the motion of parallel motion mechanism 910 may be constrained to translate parallel motion mechanism 910 in X-Y space, as shown in the exemplary embodiment of FIG. 16. The motion of parallel motion mechanism 910 may be constrained so that motion along an arc is minimized or prevented because motion along an arc through proximal joint 912 to distal joint 914 would not translate the distal end portion 917 of parallel motion mechanism 910 in X-Y space while maintaining the orientation of distal end portion 917 relative to proximal end 915. As a result, parallel motion mechanism 910 may be constrained in a substantially opposite manner to that of the wrists of the exemplary embodiments of FIGS. 3-15. That is, the wrists may be constrained to permit bending motion along an arc but minimize or prevent translation motion in X-Y space, which could result in an S-shape or the like, while a parallel motion mechanism may be constrained to permit translation motion in X-Y space but minimize or prevent bending motion along an arc.

Figure 18:
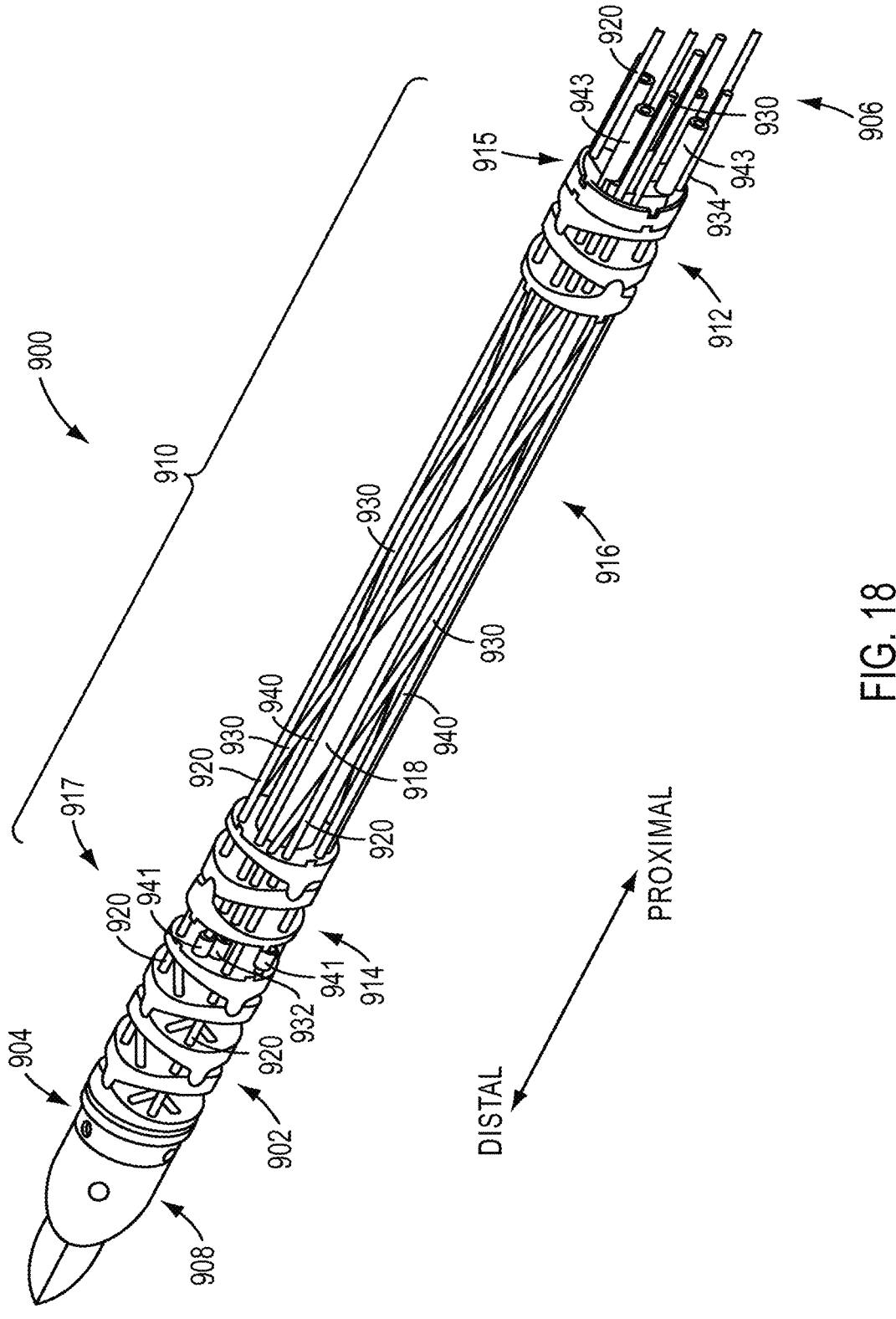
FIG. 18 shows the view of the distal portion of the surgical instrument of FIG. 16 with external surfaces removed to facilitate viewing of various internal components.

Turning to FIG. 18, the exemplary embodiment of FIG. 16 is shown with external surfaces of shaft 906 and straight section 916 of parallel motion mechanism 910 removed to reveal internal components. As shown in the exemplary embodiment of FIG. 18, straight section 916 may include a central tube 918 extending between proximal joint mechanism 912 and distal joint mechanism 914. Central tube 918 may be hollow, permitting components of an instrument to pass through the interior of central tube 918, such as to wrist 902 and/or end effector 908.

As shown in the exemplary embodiment of FIG. 18, wrist drive tendons 920 may extend from shaft 906 and parallel motion mechanism 910 to wrist 902 where wrist drive tendons 920 may be attached to a distal end of wrist 902 or distal end 904 of instrument distal portion 900 to actuate wrist 902, as discussed above with regard to the exemplary embodiment of FIG. 3. Wrist drive tendons 920 may extend over an exterior surface of central tube 918, as shown in the exemplary embodiment of FIG. 18. According to an exemplary embodiment, wrist drive tendons 920 may pass through an annular space provided between central tube 918 and an outer casing 919 (shown in FIGS. 16 and 17) of straight section 916.

An instrument further includes one or more tendons to actuate parallel motion mechanism 910. For example, parallel motion mechanism actuation members 930 may extend from shaft 906 through parallel motion mechanism 910 and be fixed to distal end 914 of parallel motion mechanism 910 so that parallel motion mechanism 910 may be actuated, such as by applying forces to tendons 930. According to an exemplary embodiment, actuation members 930 may be pull/pull actuation members or push/pull actuation members. Some parallel motion mechanisms, due to limitations on the amount of interior space within a parallel motion mechanism, may use three drive tendons to actuate the parallel motion mechanism. However, parallel motion mechanisms of the exemplary embodiments described herein may provide an increase amount of interior space due to their configurations, permitting various numbers of drive tendons to be used. For example, four actuation members 930 may be used to actuate parallel motion mechanism 910, with actuation members 930 arranged in pairs, e.g., connected to capstans, similar to the actuation members 364 of the exemplary embodiment of FIG. 4, which provides a robust construction and control for actuating drive tendons and parallel motion mechanism 910. Actuation members 930 may extend over central tube 918. According to an exemplary embodiment, actuation members 930 may pass through an annular space provided between central tube 918 and an outer casing 919 of straight section 916.

Parallel motion mechanism 910 may further include one or more constraint members fixed at opposite ends of parallel motion mechanism 910, according to an exemplary embodiment. For example, constraint tendons 940 may extend from distal end 915 of parallel motion mechanism 910 to proximal end 917, with constraint tendons 940 being fixed at distal end 915 and proximal end 917. Constraint tendons 940 may be fixed in place via, for example, welding constraint tendons 940 to a component of parallel motion mechanism 910, crimping constraint tendon 940 to another object, or by other techniques familiar to one of ordinary skill in the art. In the exemplary embodiment of FIG. 18, distal ends of constraint tendons 940 are fixed to a disk of distal joint mechanism 914 and fixed to a disk of proximal joint mechanism 912. As shown in the exemplary embodiment of FIG. 18, one end of constraint tendons 940 may be fixed by distal crimps 941 at distal end 917 of parallel motion mechanism 910 and another end of constraint tendons 940 may be fixed by proximal crimps 943 at proximal end 915 of parallel motion mechanism 910. As shown in the exemplary embodiment of FIG. 18, constraint tendons 940 may extend over an exterior surface of central tube 918. According to an exemplary embodiment, constraint tendons 940 may pass through an annular space provided between central tube 918 and an outer casing 919 (shown in FIGS. 16 and 17) of straight section 916.

Although the parallel motion mechanisms of the exemplary embodiments described herein have similar motions and functions to the embodiments described in U.S. Pat. No. 7,942,868, published May 17, 2011, and U.S. Pub. No. US 2008/0065105, published Mar. 13, 2008, the parallel motion mechanisms of the exemplary embodiments described herein have different structures, which advantageously provide more interior room for more components, such as drive tendons and/or constraint tendons, as well as smooth, precise motion of the parallel motion mechanisms.

Figure 19:
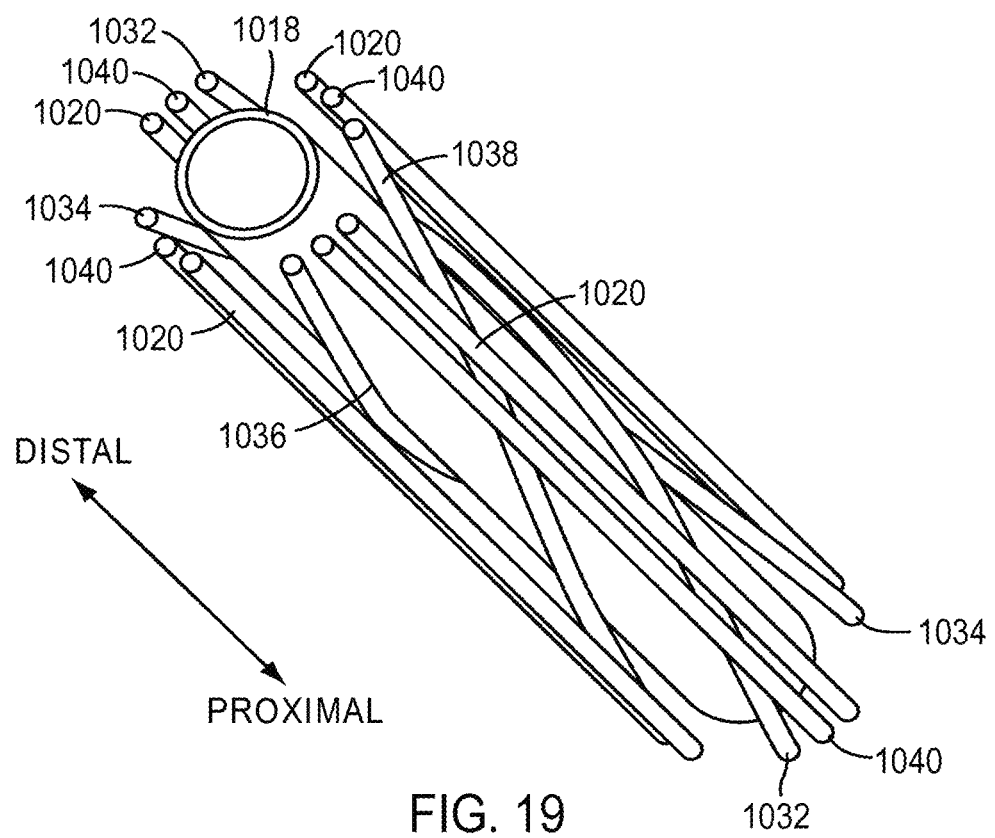
FIG. 19 is a schematic perspective view of a central tube and actuation members extending through a parallel motion mechanism, according to an exemplary embodiment.

According to an exemplary embodiment, parallel motion mechanism 910 does not include the stiffening brackets 1670 described in U.S. Pat. No. 7,942,868, resulting in more interior space within parallel motion mechanism 910. Although stiffening brackets 1670 described in U.S. Pat. No. 7,942,868 take up some interior space, the configuration of the stiffening brackets 1670 increased the tensile force applied to an actuating cable 1680 connected to a bracket 1670, with both constraint cables and actuating cables extending straight through the parallel motion mechanism. To address this, actuation members 930 of parallel motion mechanism 910 may extend along a helical path along at least a portion of parallel motion mechanism 910. This is further illustrated in the exemplary embodiment of FIG. 19, which shows a central tube 1018 of a parallel motion mechanism with wrist drive tendons 1020, constraint tendons 1040, and parallel motion mechanism drive tendons 1032, 1034, 1036, 1038. As shown FIG. 19, wrist drive tendons 1020 and constraint tendons 1040 may be substantially straight, while parallel motion mechanism drive tendons 1032, 1034, 1036, 1038 extend in helical paths about central tube 1018. According to an exemplary embodiment, parallel motion mechanism drive tendons 1032, 1034, 1036, 1038 may extend along a helical path having an angular extent of approximately 180 degrees along central tube 1018, as shown in FIG. 19. For instance, parallel motion mechanism tendons 930 in FIG. 18, including parallel motion mechanism drive tendon 934, may extend along a helical path having an angular extent of approximately 180 degrees from proximal end 915 of parallel motion mechanism 910 to distal end 917 of parallel motion mechanism 910.

Because parallel motion mechanism actuating members may extend along a helical path along at least a portion of a parallel motion mechanism, a mechanical advantage may be provided to the tendons without the use of stiffening brackets and mechanisms employed in other parallel motion mechanism designs. For example, when parallel motion mechanism 910 is actuated as shown in FIG. 17, parallel motion mechanism drive tendon 934 is on the bottom side 950 of parallel motion mechanism 910 at proximal end 915, causing a positive change in length of drive tendon 934 and additional tension to be exerted upon drive tendon 934. However, because the same drive tendon 934 extends along a helical path having an angular extent of approximately 180 degrees, drive tendon 934 is on the top side 954 of parallel motion mechanism 910 at distal end 917, causing drive tendon 934 to experience a positive change in length at distal end 917 as well, which also exerts tension upon drive tendon 934. Therefore, actuation members 930, including tendon 934, may extend along a helical path along parallel motion mechanism 910 to provide a mechanical advantage for actuating parallel motion mechanism 910, while also resulting in more interior space for components by eliminating other interior structural support elements.

In contrast to actuation members 930, constraint tendons 940 follow a substantially straight path as they extend through parallel motion mechanism 910, as shown in the exemplary embodiment of FIG. 18. As a result, when parallel motion mechanism 910 is actuated as shown in FIG. 17, constraint tendons 940 on the bottom side 950 of proximal joint mechanism 912 experience a positive change in length. Because constraint tendons 940 are fixed at opposite ends of parallel motion mechanism 910, the same constraint tendons 940 running straight along the bottom side of parallel motion mechanism 910 experience a negative change in length on bottom side 952 of distal joint mechanism 914, causing distal joint mechanism 914 and proximal joint mechanism 912 to bend in opposite manners to provide the offset but parallel positioning of distal end 917 and proximal end 915 of parallel motion mechanism 910.

As described in the exemplary embodiments of FIGS. 16-20, a parallel motion mechanism may use tendons as mechanisms to constrain motion of the parallel motion mechanism. In other exemplary embodiments, a parallel motion mechanism may include a braided structure, as described in the exemplary embodiments of FIGS. 11-15. According to an exemplary embodiment, a braided structure may replace the disks in proximal joint mechanism 912 and distal joint mechanism 914 of parallel motion mechanism 910, in a manner as described in regard to the exemplary embodiment of FIG. 11. In another exemplary embodiment, a braided structure may be placed around the disks of proximal joint mechanism 912 and distal joint mechanism 914, as described in regard to the exemplary embodiment of FIG. 15.

Although wrists and parallel motion mechanisms according to the exemplary embodiments described herein may be used separately (i.e., an instrument may include a wrist or a parallel motion mechanism), an instrument may include both a wrist and a parallel motion mechanism. When an instrument includes both a wrist and a parallel motion mechanism, the wrist may include constraint mechanism, such as constraint tendons, separate from constraint mechanisms, such as constraint tendons, of the parallel motion mechanism. For example, the wrist includes a first constraint mechanism, such as a first set of one or more constraint tendons, and the parallel motion mechanism includes a second constraint mechanism, such as a second set of one or more constraint tendons. According to an exemplary embodiment, when the wrist and parallel motion mechanism have separate constraint tendons, the constraint tendons of the wrist and parallel motion mechanism may differ, such as by having differing diameters, or other structural or material differences, which may be chosen to achieve desired motion effects, for example.

According to another embodiment, the wrist and parallel motion mechanism use the same constraint mechanism, such as the same constraint tendons. Using the same constraint mechanism in the wrist and parallel motion mechanism may be efficient for conserving the interior space of an instrument to use the same constraint mechanisms for both a wrist and a parallel motion mechanism.

Figure 21:
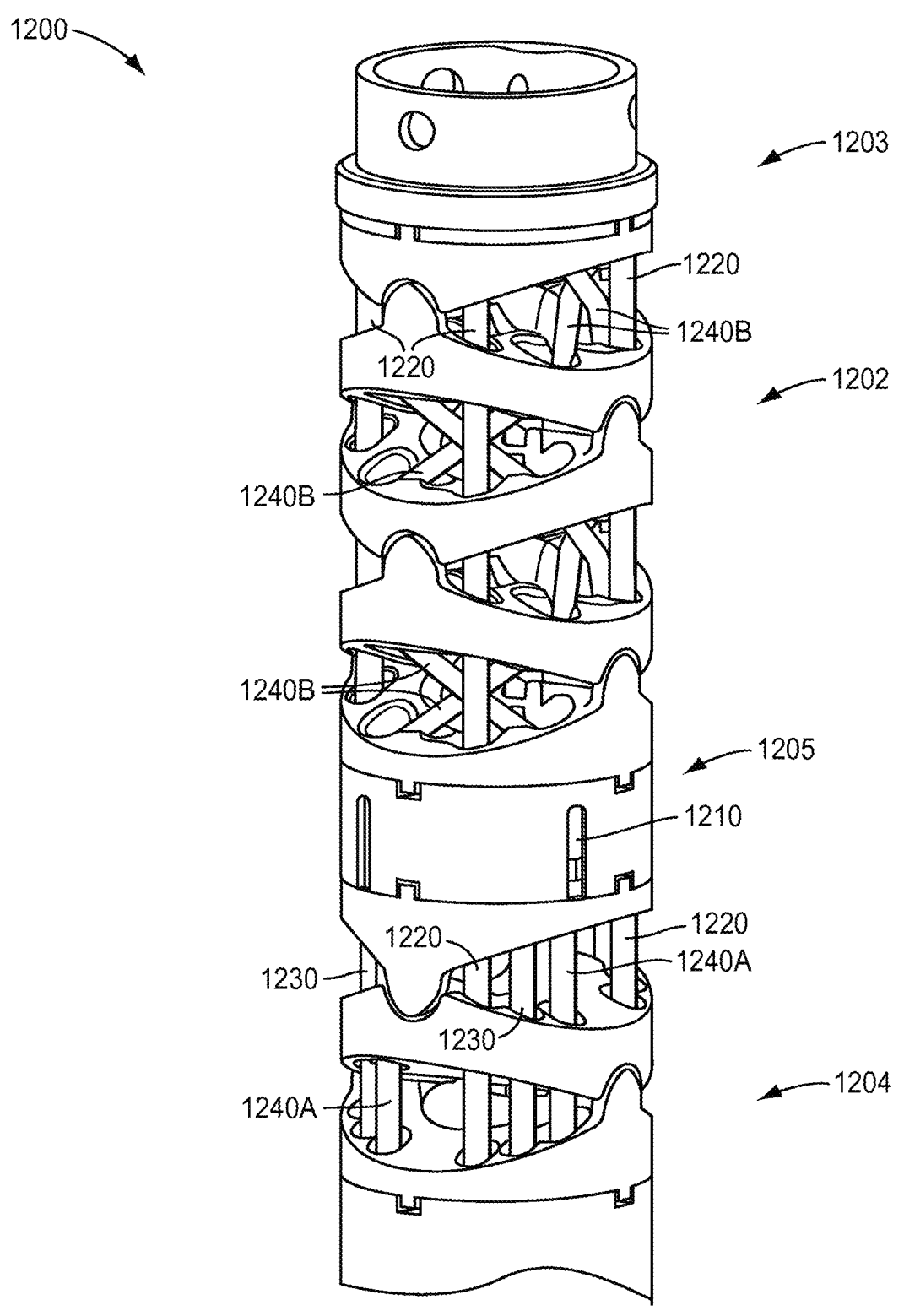
FIG. 21 is a partial perspective view of a distal portion of a surgical instrument including a wrist and a parallel motion mechanism with shared constraint mechanism(s), according to an exemplary embodiment.

With reference to FIG. 21, a partial view is shown of a distal end portion 1200 of an instrument that includes a wrist 1202 and a parallel motion mechanism 1204, which may be configured according to the exemplary embodiments of FIGS. 16-20. Wrist 1202 may be configured according to the exemplary embodiments of FIGS. 3-14 and parallel motion mechanism 1204 may be configured according to the exemplary embodiments of FIGS. 15-19. As shown in FIG. 21, wrist 1202 may be located distally to parallel motion mechanism 1204. Wrist drive tendons 1220 may extend through parallel motion mechanism 1204 to wrist 1202 and through wrist 1202 to a distal end of wrist 1202 or distal end 1203 of instrument where wrist drive tendons 1220 are fixed to actuate wrist 1202. Parallel motion mechanism drive tendons 1230 extend through parallel motion mechanism 1204 and may be fixed at a distal end of parallel motion mechanism 1204.

According to an exemplary embodiment, wrist 1202 and parallel motion mechanism 1204 share constraint tendons that constrain motion of both wrist 1202 and parallel motion mechanism 1204. For example, constraint tendons for both wrist 1202 and parallel motion mechanism 1204 include a first portion of constraint tendons 1240A that extend through parallel motion mechanism 1204, are fixed (such as, for example, at a distal end of parallel motion mechanism 1204, at proximal end of wrist 1202, or between parallel motion mechanism 1204 and wrist 1202, such as via crimps 1210 discussed below) have a second portion of constraint tendons 1240B that extend through wrist 1202, and are fixed again. The first and second portions 1240A, 1240B are of the same, continuous constraint tendons, so that the same constraint tendons (portions 1240A, 1240B) may be used to constrain both wrist 1202 and parallel motion mechanism 1204. For instance, the constraint tendons may be fixed at a distal end of parallel motion mechanism 1204, a proximal end of wrist 1202, or in a connection region 1205 between wrist 1202 and parallel motion mechanism 1204, as shown in the exemplary embodiment of FIG. 21. Thus, one set of constraint tendons (including portions 1240A, 1240B) may be used to constrain the motion of both wrist 1202 and parallel motion mechanism 1204, which provides an efficient use of interior space of an instrument.

According to an exemplary embodiment, wrist 1202 and parallel motion mechanism 1204 have separate constraint tendons that respectively constrain motion of wrist 1202 and parallel motion mechanism 1204. For example, first portion of constraint tendons 1240A represents a first set of one or more constraint tendons and second portion of constraint tendons 1240B represents a second set of one or more constraint tendons separate from the first portion of constraint tendons 1240A. When wrist 1202 and parallel motion mechanism 1204 have different constraint tendons, the constraint tendons for parallel motion mechanism 1204 (e.g., first portion 1240A) may be fixed, for example, at a distal end of parallel motion mechanism 1204, at proximal end of wrist 1202, or between parallel motion mechanism 1204 and wrist 1202, and the constraint tendons for wrist 1202 (e.g., second portion 1240B) may be fixed at, for example, at a distal end of parallel motion mechanism 1204, at proximal end of wrist 1202, or between parallel motion mechanism 1204 and wrist 1202, extend through wrist 1202, and be fixed at a distal end of wrist 1202.

The constraint tendons may be fixed, according to the exemplary embodiments of FIGS. 3-20. For instance, the first portion of constraint tendons 1240A may extend through parallel motion mechanism 1204, through crimps 1210 that fix constraint tendons 1240 relative to instrument distal portion 1200, and end at crimps, with the second portion of constraint tendons 1240B separately extending through wrist 1202 (such as when separate tendons constrain wrist 1202 and parallel motion mechanism 1204), or the constraint tendons may continue from crimps 120 through wrist 1202 as a second portion 1240B of the same constraint tendons that extend through both parallel motion mechanism 1204 and wrist 1202. Further, the constraint tendons may be arranged according to the exemplary embodiments of FIGS. 3-20, with, for example, the constraint tendons (e.g., portions 1240A, 1240B) extending in a substantially straight direction through parallel motion mechanism 1204 and extending along a helical path through at least a portion of wrist 1202.

The exemplary embodiments and methods described herein have been described as being utilized with surgical instruments for teleoperated surgical systems. However, the exemplary embodiments and methods described herein may be used with other surgical devices, such as laparoscopic instruments and other manual (e.g., hand held) instruments, and non-surgical devices, such as devices that include any of a variety of actuated articulatable members, including but not limited to wrists and/or parallel motion mechanisms, whether the devices are teleoperated, remote controlled, or manually operated.

By providing surgical instruments with constraint mechanisms according to the exemplary embodiments described herein, articulatable members are provided that have simpler force transmission mechanisms that are easier to control and less costly to manufacture, while the articulatable members provide substantially repeatable, smooth, precise motions.

Further modifications and alternative embodiments will be apparent to those of ordinary skill in the art in view of the disclosure herein. For example, the systems and the methods may include additional components or steps that were omitted from the diagrams and description for clarity of operation. Accordingly, this description is to be construed as illustrative only and is for the purpose of teaching those skilled in the art the general manner of carrying out the present teachings. It is to be understood that the various embodiments shown and described herein are to be taken as exemplary. Elements and materials, and arrangements of those elements and materials, may be substituted for those illustrated and described herein, parts and processes may be reversed, and certain features of the present teachings may be utilized independently, all as would be apparent to one skilled in the art after having the benefit of the description herein. Changes may be made in the elements described herein without departing from the spirit and scope of the present teachings and following claims.

It is to be understood that the particular examples and embodiments set forth herein are non-limiting, and modifications to structure, dimensions, materials, and methodologies may be made without departing from the scope of the present teachings.

Other embodiments in accordance with the present disclosure will be apparent to those skilled in the art from consideration of the specification and practice of the invention disclosed herein. It is intended that the specification and examples be considered as exemplary only, with a true scope and spirit being indicated by the following claims.

What is claimed is:

1. An articulatable member, comprising:
a plurality of links extending in a series from a proximal end link to a distal end link, adjacent links of the plurality of links being pivotably coupled to form joints between the adjacent links;
a first cable extending between the proximal end link and the distal end link; and
a second cable extending between and fixed to the proximal end link and the distal end link;
wherein each link of the plurality of links comprises an annular shape defining a central aperture and an outer perimeter;
wherein the first cable extends through a first aperture in each link of the plurality of links, the first aperture located between the central aperture and the outer perimeter and radially inward a first distance from the outer perimeter of each link of the plurality of links;
wherein the second cable extends through a second aperture in each link of the plurality of links, the second aperture located between the central aperture and the outer perimeter and radially inward a second distance greater than the first distance from the outer perimeter of each link of the plurality of links; and
wherein the second cable follows a helical path along at least a portion of the articulatable member from the proximal end link to the distal end link as the second cable extends through the second aperture in each of the links.

2. The articulatable member of claim 1, wherein the first cable comprises an actuation cable configured to articulate the articulatable member in response to a tensile force applied to the actuation cable.

3. The articulatable member of claim 2, wherein the actuation cable follows a straight path along the articulatable member.

4. The articulatable member claim 1, wherein the second cable comprises a constraint member configured to passively constrain articulation of the articulatable member.

5. The articulatable member of claim 1, wherein:
the articulatable member comprises a third cable extending between and fixed to the distal end link and the proximal end link;
the third cable extends through a third aperture in each link of the plurality of links; and
the third aperture is positioned radially inward the second distance from the outer perimeter of each link of the plurality of links and spaced 180 degrees from the second aperture around a circumference of each link of the plurality of links.

6. The articulatable member of claim 1, wherein the first aperture and the second aperture are spaced 90 degrees from one another around a circumference of each link of the plurality of links.

7. The articulatable member of claim 1, wherein the helical path extends at least 180 degrees around a circumference of the articulatable member from the proximal end link and the distal end link.

8. The articulatable member of claim 1, wherein the helical path extends at least 360 degrees around a circumference of the articulatable member from the proximal end link and the distal end link.

9. An articulatable member, comprising:
a plurality of links extending in a series from a proximal end link to a distal end link, adjacent links of the plurality of links being pivotably coupled to form joints between the adjacent links, and each link of the plurality of links having a central longitudinal axis and an outer lateral surface;
a first constraint member extending between and fixed to the proximal end link and the distal end link, the first constraint member following a first, right-handed helical path spiraling along at least a portion of the articulatable member; and
a second constraint member extending between and fixed to the proximal end link and the distal end link, the second constraint member following a second, left-handed helical path spiraling along at least the portion of the articulatable member,
wherein the first and second constraint members pass through respective enclosed apertures in each of the plurality of links at locations between the central longitudinal axis and the outer lateral surface.

10. The articulatable member claim 9, wherein the plurality of links comprises:
a first link, a second link adjacent the first link, a third link adjacent the second link, a fourth link adjacent the third link, and a fifth link adjacent the fourth link;
a first joint between the first link and the second link, the first joint permitting relative rotation of the first and second links about a first axis;
a second joint between the second link and the third link, the second joint permitting relative rotation of the second and third links about a second axis orthogonal to the first axis;
a third joint between the third link and the fourth link, the third joint permitting relative rotation of the third and fourth links about the first axis; and
a fourth joint between the fourth link and the fifth link, the fourth joint permitting relative rotation of the fourth and fifth links about the second axis.

11. The articulatable member claim 9, wherein the plurality of links comprises:
a first link, a second link adjacent the first link, a third link adjacent the second link, a fourth link adjacent the third link, and a fifth link adjacent the fourth link;
a first joint between the first link and the second link, the first joint permitting relative rotation of the first and second links about a first axis;

a second joint between the second link and the third link, the second joint permitting relative rotation of the second and third links about a second axis orthogonal to the first axis;
a third joint between the third link and the fourth link, the third joint permitting relative rotation of the third and fourth links about the second axis; and
a fourth joint between the fourth link and the fifth link, the fourth joint permitting relative rotation of the fourth and fifth links about the first axis.

12. The articulatable member of claim 9, wherein:
the first constraint member is laterally spaced from the central longitudinal axis of the articulatable member a first distance;
the second constraint member is laterally spaced from the central longitudinal axis a second distance; and
the second distance is greater than the first distance.

13. The articulatable member of claim 9, wherein the first constraint member extends through a first enclosed aperture of the respective enclosed apertures, in a link of the plurality of links, the first enclosed aperture being radially offset from the central longitudinal axis of the link and positioned radially inward from the outer lateral surface of the link by a first distance.

14. The articulatable member of claim 13, wherein the second constraint member extends through a second enclosed aperture of the respective enclosed apertures, in the link of the plurality of links, the second enclosed aperture being radially offset from the central longitudinal axis of the link and positioned radially inward from the outer lateral surface of the link by a second distance, wherein the second distance is greater than the first distance.

15. The articulatable member of claim 9, wherein the first helical path and the second helical path extend an equal amount around the articulatable member.

16. The articulatable member of claim 9, wherein the first helical path and the second helical path each extend at least 180 degrees around the articulatable member from the proximal end link to the distal end link.

17. The articulatable member of claim 9, wherein the first helical path and the second helical path each extend at least 360 degrees around the articulatable member from the proximal end link to the distal end link.

18. The articulatable member of claim 5, wherein the third cable follows a helical path along at least a portion of the articulatable member from the proximal end link to the distal end link as it extends through the third aperture in each of the links.

19. The articulatable member of claim 18, wherein the helical paths of the second cable and the third cable spiral in opposite directions from each other.

20. The articulatable member of claim 1, wherein in each link of the plurality of links comprises:
a first plurality of apertures, including the first aperture, spaced apart around the link and located radially inward the first distance from the outer perimeter; and
a second plurality of apertures, including the second aperture, spaced apart around the link and located radially inward the second distance from the outer perimeter.

* * * * *